(12) United States Patent
Sasada et al.

(10) Patent No.: US 9,059,410 B2
(45) Date of Patent: Jun. 16, 2015

(54) LIQUID CRYSTALLINE ORGANIC SEMICONDUCTOR MATERIAL AND ORGANIC SEMICONDUCTOR DEVICE USING SAME

(75) Inventors: Yasuyuki Sasada, Ichihara (JP); Yo Shimizu, Ikeda (JP); Hirosato Monobe, Ikeda (JP)

(73) Assignees: NATIONAL INSTITUTE OF ADVANCED INDUSTRIAL SCIENCE AND TECHNOLOGY, Tsukuba-shi (JP); JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 1519 days.

(21) Appl. No.: 11/819,580

(22) Filed: Jun. 28, 2007

(65) Prior Publication Data

US 2008/0058544 A1    Mar. 6, 2008

(30) Foreign Application Priority Data

Aug. 30, 2006  (JP) .................. 2006-233429
Mar. 8, 2007   (JP) .................. 2007-058990

(51) Int. Cl.
    C09K 19/52    (2006.01)
    C09K 19/32    (2006.01)
    C07C 69/92    (2006.01)
    H01L 51/00    (2006.01)

(52) U.S. Cl.
    CPC ............ *H01L 51/0054* (2013.01); *C07C 69/92* (2013.01); *C09K 19/32* (2013.01); *C09K 2019/328* (2013.01)

(58) Field of Classification Search
    CPC .................. C09K 19/584; C09K 2019/328
    USPC .......... 252/500, 299.3; 428/1.4; 560/1, 55, 62
    See application file for complete search history.

(56) References Cited

U.S. PATENT DOCUMENTS

2004/0151846 A1    8/2004   Aminaka et al.

FOREIGN PATENT DOCUMENTS

| DE | 19534494 A1 | 3/1997 |
|---|---|---|
| EP | 0529439 A1 | 3/1993 |
| EP | 0676652 A2 | 10/1995 |
| JP | 8-181364 A | 7/1996 |
| JP | 2005-12025 A | 1/2005 |
| JP | 2006-222306 A | 8/2006 |
| WO | WO 94/29263 A1 | 12/1994 |

OTHER PUBLICATIONS

European Search Report dated Dec. 21, 2007, issued in corresponding European Patent Application No. 07252649.
Dahn, U. et al.; "Fluoroalkylated discotic liquid crystals"; Liquid Crystals, vol. 19, No. 6, 1995, pp. 759-764.
Adam, D. et al.; "Fast photoconduction in the highly ordered columnar phase of a discotic liquid crystal"; Letters to Nature, vol. 371, No. 6493, 1994, pp. 141-143.
Fimmen, W. et al.; "A re-entrant $Col_{ho}$phase"; Liquid Crystals, vol. 23, No. 4, 1997, pp. 569-573.
Praefcke, K. et al.; "Core-halogenated, helical-chiral triphenylene-based columnar liquid crystals"; Liquid Crystals, vol. 22, No. 2, 1997, pp. 113-119.
D. Haarer et al., Letters to Nature "Nature", vol. 371, Sep. 8, 1994, pp. 141-143.
C. Vauchier et al., Mol. Liq. Cryst., "Orientation of Discotic Mesophases" vol. 66, 1981, pp. 103-114.
Y. Sasada et al., Chemistry Letters "Aromatic Fluorination Effect on the Mesomorphic Properties of Discotic Liquid Crystal of Alkoxybenzoyloxytriphenylene" vol. 36, No. 5, 2007, pp. 584-585.
Y. Sasada et al., $9^{th}$ European Conference of Liquid Crystal "Aromatic Fluorination Effect on the Mesomorphic Properties of Discotic Liquid Crystal of Alkoxybenzoyloxytriphenylene" 2007, PA22.
Y. Sasada et al., The Chemical Society of Japan, 2007 2E2-04.

*Primary Examiner* — Susanna Moore
(74) *Attorney, Agent, or Firm* — Westerman, Hattori, Daniels & Adrian, LLP

(57) ABSTRACT

The present invention provides a novel organic semiconductor material that affords efficient charge transport, under a wider range of conditions, by increasing the temperature stability and expanding the temperature range of the organic semiconductor material. In an organic semiconductor material comprising a liquid crystalline compound having substituents on the periphery of a rigid plate-like central structure, the substituents have a fluorinated phenylene group, and columns in which the molecules of the compound are accumulated in a stack are aligned hexagonally.

11 Claims, 1 Drawing Sheet

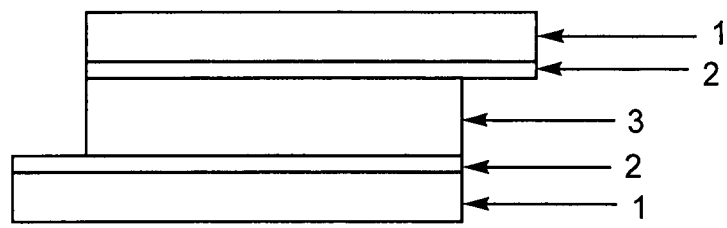

LIQUID CRYSTALLINE ORGANIC SEMICONDUCTOR MATERIAL AND ORGANIC SEMICONDUCTOR DEVICE USING SAME

FIELD OF THE INVENTION

The present invention relates to a liquid crystalline organic semiconductor material wherein columns in which molecules having a fluoro-substituted phenylene ring are accumulated in a stack are aligned hexagonally.

DESCRIPTION OF THE RELATED ART

Among new rigid plate-like discotic liquid crystals there have been reports on compounds having a triphenylene structure that can impart an extremely high charge mobility, of $10^{-1}$ cm$^2$/V·s (D. Haarer et al, Nature, 371, 141(1994)), and which are interesting as new organic semiconductors.

When a discotic liquid crystal is used as an organic semiconductor, the columnar phase, in particular the hexagonal columnar phase (Col$_h$ phase) is a liquid crystal phase in which molecular columns are aligned filling a hexagonal crystal column shape, being a preferred liquid crystal when a discotic liquid crystal is used in organic semiconductors.

However, even compounds that exhibit a Col$_h$ phase have so only within a predetermined narrow temperature range. Also, because Col$_h$ phase is a high-order liquid crystal phase, when in a high-temperature region, the liquid crystal changes into an isotropic liquid (Iso), all of which has precluded heretofore high-speed charge transport.

In the field of rod-like liquid crystals, meanwhile, compounds having fluoro-substituted phenylene rings are characterized by the high electronegativity and the small Van der Waals radius of the fluorine atoms, and hence have been often reported to exhibit large dielectric anisotropy values that do not impair liquid crystallinity.

International Patent Application Publication Number WO94/29263 and Mol. Cryst. Liq. Cryst., 1998, 66, 103-114 disclose discotic liquid crystals of compounds having a fluoro-substituted phenylene ring.

International Patent Application Publication Number W/O 94/29263 does not describe at all that the compounds having fluoro-substituted phenylene rings form a columnar phase, let alone an hexagonal columnar phase, nor does it hint in any way at the use of these compounds as organic semiconductor materials.

Although Mol. Cryst. Liq. Cryst., 1998, 66, 103-114 describes that liquid crystal phases exhibited by compounds having fluoro-substituted phenylene rings are a columnar phase, the document does not describe that the columnar phase is a Col$_h$ phase, and it provides almost no detailed data on the columnar phase (columnar phase type, liquid crystal phase temperature range and the like). Also, Mol. Cryst. Liq. Cryst., 1998, 66, 103-114 does not hint in any way at the use of the compounds as an organic semiconductor material.

SUMMARY OF THE INVENTION

An object of the present invention is to provide a novel organic semiconductor material that affords efficient charge transport by increasing the temperature stability and expanding the temperature range of the organic semiconductor material.

As a result of diligent research, the inventors perfected the present invention upon finding that introducing a fluoro-substituted phenylene ring at least one position around a rigid plate-like central structure has the effect of inducing a structure, in particular a Col$_h$ phase, in which columns of stacked molecules adopt a hexagonal crystal-like alignment, thus expanding the temperature range, increasing thermal stability, and enabling efficient charge transport even in a wide, high-temperature region.

As described below, specifically, the present invention provides a liquid crystalline organic semiconductor material having a fluorinated phenylene group. Examples of terminal groups, rings and bonding groups of the organic semiconductor material (1) are also explained below.

[1] An organic semiconductor material comprising a liquid crystalline compound having substituents on the periphery of a rigid plate-like central structure, wherein the substituents have a fluorinated phenylene group, and columns in which the compound is accumulated in a stack are aligned in the shape of a hexagonal crystal.

[2] The organic semiconductor material in [1], wherein the central structure comprises a conjugated n electron system.

[3] The organic semiconductor material in [1], wherein the conjugated n electron system is selected from the group consisting of triphenylene, coronene, benzocoronene, phthalocyanine, porphyrin, truxene, pyran, tricycloquinazoline, phenyl acetylene, calixarene, pyrene, perylene, oligothiophene, decacyclene and rufigallol structures.

[4] The organic semiconductor material in [1] comprising at least one compound selected from the group of compounds represented by formula (1):

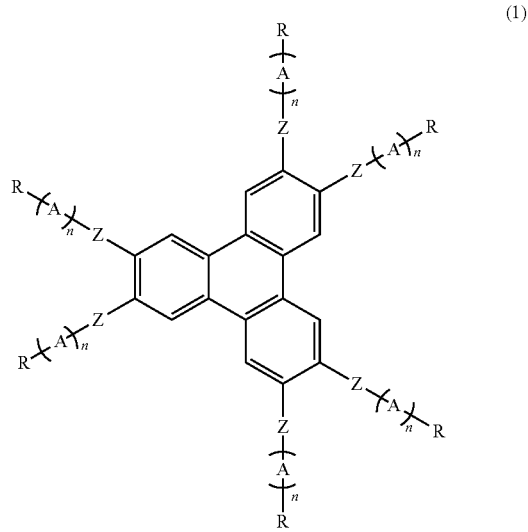

(1)

In formula (1), R is independently hydrogen, a C1 to C24 linear or branched alkyl; in the alkyl, any —CH$_2$— may be replaced by —O—, —S—, —CO— or —SiH$_2$—, any —(CH$_2$)$_2$— may be replaced by —CH=CH— or —C≡C—, and any hydrogen may be replaced by a halogen.

The meaning of the phrase "in the alkyl, any —CH$_2$— may be replaced by —O— or the like, any —(CH$_2$)$_2$— may be replaced by —CH=CH— or the like" is exemplified below. In CH$_3$(CH$_2$)$_3$—, examples where any —CH$_2$— is replaced by —O—, and in which —(CH$_2$)$_2$— is replaced by —CH=CH— include, for instance, CH$_3$(CH$_2$)O—, CH$_3$—O—(CH$_2$)$_2$—, CH$_3$—O—CH$_2$—O—, H$_2$C=CH—(CH$_2$)$_2$—, CH$_3$—CH=CH—CH$_2$—, CH$_3$—CH=CH—O—. The term "any" means "at least one, arbitrarily selected". In terms of compound stability, CH$_3$—O—CH$_2$—

O—, where oxygen is not adjacent to oxygen, is preferred to —CH$_2$—O—O—CH$_2$—, where oxygen and oxygen are adjacent.

Examples of R include, for instance, hydrogen, fluorine, chlorine, alkyl, alkoxy, alkoxyalkyl, alkoxyalkoxy, alkylthio, alkylthioalkyl, alkylthioalkoxy, acyl, acylalkyl, acyloxy, acyloxyalkyl, alkoxycarbonyl, alkoxycarbonylalkyl, alkenyl, alkenyloxy, alkenyloxyalkyl, alkoxyalkenyl, alkynyl, alkynyloxy, silaalkyl, and disilaalkyl. Preferably, at least one hydrogen of these compounds is substituted with a halogen. Preferably, the halogen is fluorine and chlorine. More preferably, the halogen is fluorine. These groups are preferably linear rather than branched, although in terms of lowering the clearing point, branched groups are preferable to linear ones. Also, when R has optical activity, branched groups are preferable.

Preferably, R is fluorine, alkyl, alkoxy, alkoxyalkyl, alkynyl, alkylthio, alkylthioalkyl, polyfluoroalkyl, and polyfluoroalkoxy.

More preferably, R is alkyl, alkoxy, alkylthio, polyfluoroalkyl, and polyfluoroalkoxy.

Most preferably, R is alkyl, alkoxy, and alkylthio.

Specific examples of alkyl include, for instance, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{24}$, —C$_{13}$H$_{27}$, —C$_{14}$H$_{29}$, and —C$_{15}$H$_{31}$.

Specific examples of alkoxy include, for instance, —OC$_4$H$_9$, —OC$_5$H$_{11}$, —OCH(CH$_3$)C$_3$H$_7$, —OC$_6$H$_{13}$, —OCH(CH$_3$)C$_4$H$_9$, —OC$_7$H$_{15}$, —OCH(CH$_3$)C$_5$H$_{11}$, —OC$_8$H$_{17}$, —OCH(CH$_3$)C$_6$H$_{13}$—OC$_9$H$_{19}$, —OCH(CH$_3$)C$_7$H$_{15}$, —OC$_{10}$H$_{21}$, —OCH(CH$_3$)C$_8$H$_{17}$, —OC$_{11}$H$_{23}$, —OCH(CH$_3$)C$_9$H$_{19}$, —OC$_{12}$H$_{24}$, —OCH(CH$_3$)C$_{10}$H$_{21}$, —OC$_{13}$H$_{27}$, —OC$_{14}$H$_{29}$, and —OC$_{15}$H$_{31}$.

Specific examples of alkoxyalkyl include, for instance, —(CH$_2$)$_2$—O—CH$_3$, —(CH$_2$)$_2$—O—C$_2$H$_5$, —(CH$_2$)$_3$—O—CH$_3$, —(CH$_2$)$_2$—O—(CH$_2$)$_2$CH$_3$, —(CH$_2$)$_3$—O—C$_2$H$_5$, —(CH$_2$)$_2$—O—(CH$_2$)$_3$CH$_3$, —(CH$_2$)$_3$—O—(CH$_2$)$_2$CH$_3$, —(CH$_2$)$_4$—O—C$_2$H$_5$, —(CH$_2$)$_2$—O—(CH$_2$)$_4$—CH$_3$, —(CH$_2$)$_3$—O—(CH$_2$)$_3$CH$_3$, —(CH$_2$)$_4$—O—(CH$_2$)$_2$CH$_3$, —(CH$_2$)$_5$—O—C$_2$H$_5$, and —(CH$_2$)$_6$—O—CH$_3$.

Specific examples of alkenyl include, for instance, —CH$_2$CH═CHCH$_3$, —(CH$_2$)$_2$CH═CH$_2$, —CH$_2$CH═CHC$_2$H$_5$, —(CH$_2$)$_2$CH═CHCH$_3$, —(CH$_2$)$_3$CH═CH$_2$, —CH$_2$CH═CH(CH$_2$)$_2$CH$_3$, —(CH$_2$)$_2$CH═CHC$_2$H$_5$, —(CH$_2$)$_3$CH═CHCH$_3$, —(CH$_2$)$_4$CH═CH$_2$, —CH$_2$CH═CH(CH$_2$)$_3$CH$_3$, —(CH$_2$)$_2$CH═CH(CH$_2$)$_2$CH$_3$, —(CH$_2$)$_3$CH═CHC$_2$H$_5$, —(CH$_2$)$_4$CH═CHCH$_3$, —(CH$_2$)$_5$CH═CH$_2$, —CH$_2$CH═CH(CH$_2$)$_5$CH$_3$, —(CH$_2$)$_2$CH═CH(CH$_2$)$_4$—CH$_3$, —(CH$_2$)$_3$CH═CH(CH$_2$)$_3$CH$_3$, —(CH$_2$)$_4$—CH═CH(CH$_2$)$_2$CH$_3$, —(CH$_2$)$_5$CH═CHC$_2$H$_5$, —(CH$_2$)$_6$CH═CHCH$_3$, and —(CH$_2$)$_7$CH═CH$_2$.

Specific examples of alkenyloxy include, for instance, —OCH$_2$CH═CHCH$_3$, —O(CH$_2$)$_2$CH═CH$_2$, —OCH$_2$CH═CHC$_2$H$_5$, —O(CH$_2$)$_2$CH═CHCH$_3$, —O(CH$_2$)$_3$CH═CH$_2$, —OCH$_2$CH═CH(CH$_2$)$_2$CH$_3$, —O(CH$_2$)$_2$CH═CHC$_2$H$_5$, —O(CH$_2$)$_3$CH═CHCH$_3$, —O(CH$_2$)$_4$—CH═CH$_2$, —OCH$_2$CH═CH(CH$_2$)$_3$CH$_3$, —O(CH$_2$)$_2$CH═CH(CH$_2$)$_2$CH$_3$, —O(CH$_2$)$_3$CH═CHC$_2$H$_5$, —O(CH$_2$)$_4$—CH═CHCH$_3$, —O(CH$_2$)$_5$CH═CH$_2$, —OCH$_2$CH═CH(CH$_2$)$_5$CH$_3$, —O(CH$_2$)$_2$CH═CH(CH$_2$)$_4$—CH$_3$, —O(CH$_2$)$_3$CH═CH(CH$_2$)$_3$CH$_3$, —O(CH$_2$)$_4$—CH═CH(CH$_2$)$_2$CH$_3$, —O(CH$_2$)$_5$CH═CHC$_2$H$_5$, —O(CH$_2$)$_6$CH═CHCH$_3$, and —O(CH$_2$)$_7$CH═CH$_2$.

Specific examples of alkynyl include, for instance, —C≡CC$_2$H$_5$, —C≡C(CH$_2$)$_2$CH$_3$, —C≡C(CH$_2$)$_3$CH$_3$, —C≡C(CH$_2$)$_4$—CH$_3$, —C≡C(CH$_2$)$_5$CH$_3$, —C≡C(CH$_2$)$_6$CH$_3$, and —C≡C(CH$_2$)$_7$CH$_3$.

Specific examples of alkylthio include, for instance, —SC$_4$H$_9$, —SC$_5$H$_{11}$, —SCH(CH$_3$)C$_3$H$_7$, —SC$_6$H$_{13}$, —SCH(CH$_3$)C$_4$H$_9$, —SC$_7$H$_{15}$, —SCH(CH$_3$)C$_5$H$_{11}$, —SC$_8$H$_{17}$, —SCH(CH$_3$)C$_6$H$_{13}$, —SC$_9$H$_{19}$, —SCH(CH$_3$)C$_7$H$_{15}$, —SC$_{10}$H$_{21}$, —SCH(CH$_3$)C$_8$H$_{17}$, —SC$_{11}$H$_{23}$, —SCH(CH$_3$)C$_9$H$_{19}$, —SC$_{12}$H$_{24}$, —SCH(CH$_3$)C$_{10}$H$_{21}$, —SC$_{13}$H$_{27}$, —SC$_{14}$H$_{29}$, and —SC$_{15}$H$_{31}$.

Specific examples of alkylthioalkyl is, for instance, —(CH$_2$)$_2$—S—CH$_3$, —(CH$_2$)$_2$—S—C$_2$H$_5$, —(CH$_2$)$_3$—S—CH$_3$, —(CH$_2$)$_2$—S—(CH$_2$)$_2$CH$_3$, —(CH$_2$)$_3$—S—C$_2$H$_5$, —(CH$_2$)$_2$—S—(CH$_2$)$_3$CH$_3$, —(CH$_2$)$_3$—S—(CH$_2$)$_2$CH$_3$, —(CH$_2$)$_4$—S—C$_2$H$_5$, —(CH$_2$)$_2$—S—(CH$_2$)$_4$—CH$_3$, —(CH$_2$)$_3$—S—(CH$_2$)$_3$CH$_3$, —(CH$_2$)$_4$—S—(CH$_2$)$_2$CH$_3$, —(CH$_2$)$_5$—S—C$_2$H$_5$, and —(CH$_2$)$_6$—S—CH$_3$.

An alkyl in which at least one hydrogen is substituted with a halogen is, for instance, —(CH$_2$)$_3$CF$_3$, —(CH$_2$)$_3$CH$_2$F, —(CH$_2$)$_3$CF$_2$CF$_3$, —(CH$_2$)$_3$(CF$_2$)$_2$CF$_3$, —CH$_2$CHF(CH$_2$)$_3$CH$_3$, —(CH$_2$)$_3$(CF$_2$)$_3$CF$_3$, —CH$_2$CHF(CH$_2$)$_4$—CH$_3$, —(CH$_2$)$_3$(CF$_2$)$_4$CF$_3$, —CH$_2$CHF(CH$_2$)$_5$CH$_3$, —(CH$_2$)$_3$(CF$_2$)$_5$CF$_3$, —CH$_2$CHF(CH$_2$)$_6$CH$_3$, —(CH$_2$)$_3$(CF$_2$)$_6$CF$_3$, and —CH$_2$CHF(CH$_2$)$_7$CH$_3$.

An alkoxy in which at least one hydrogen is substituted with a halogen is, for instance, —OCH$_2$)$_3$CF$_3$, —O(CH$_2$)$_3$CH$_2$F, —O(CH$_2$)$_3$CF$_2$CF$_3$, —O(CH$_2$)$_3$(CF$_2$)$_2$CF$_3$, —OCH$_2$CHF(CH$_2$)$_3$CH$_3$, —O(CH$_2$)$_3$(CF$_2$)$_3$CF$_3$, —OCH$_2$CHF(CH$_2$)$_4$—CH$_3$, —O(CH$_2$)$_3$(CF$_2$)$_4$CF$_3$, —OCH$_2$CHF(CH$_2$)$_5$CH$_3$, —O(CH$_2$)$_3$(CF$_2$)$_5$CF$_3$, —OCH$_2$CHF(CH$_2$)$_6$CH$_3$, —O(CH$_2$)$_3$(CF$_2$)$_6$CF$_3$, and —OCH$_2$CHF(CH$_2$)$_7$CH$_3$.

An alkenyl in which at least one hydrogen is substituted with a halogen is, for instance, —CH$_2$CF═CFCF$_3$, —(CH$_2$)$_2$CH═CF$_2$, —CH$_2$CF═CFC$_2$F$_5$, —(CH$_2$)$_2$CF═CFCF$_3$, —(CH$_2$)$_3$CH═CF$_2$, —CH$_2$CF═CF(CF$_2$)$_2$CF$_3$, —(CH$_2$)$_2$CF═CFC$_2$F$_5$, —(CH$_2$)$_3$CF═CFCF$_3$, —(CH$_2$)$_4$—CH═CF$_2$, —CH$_2$CF═CF(CF$_2$)$_3$CF$_3$, —(CH$_2$)$_2$CF═CF(CF$_2$)$_2$CF$_3$, —(CH$_2$)$_3$CF═CFC$_2$F$_5$, —(CH$_2$)$_4$CF═CFCF$_3$, —(CH$_2$)$_5$CH═CF$_2$, —CH$_2$CF═CF(CF$_2$)$_5$CF$_3$, —(CH$_2$)$_2$CF═CF(CF$_2$)$_4$CF$_3$, —(CH$_2$)$_3$CF═CF(CF$_2$)$_3$CF$_3$, —(CH$_2$)$_4$CF═CF(CF$_2$)$_2$CF$_3$, —(CH$_2$)$_5$CF═CFC$_2$F$_5$, —(CH$_2$)$_6$CF═CFCF$_3$, and —(CH$_2$)$_7$CH═CF$_2$.

Preferably, R is, for instance, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{24}$, —OC$_4$H$_9$, —OC$_5$H$_{11}$, —OCH(CH$_3$)C$_3$H$_7$, —OC$_6$H$_{13}$, —OCH(CH$_3$)C$_4$H$_9$, —OC$_7$H$_{15}$, —OCH(CH$_3$)C$_5$H$_{11}$, —OC$_8$H$_{17}$, —OCH(CH$_3$)C$_6$H$_{13}$—OC$_9$H$_{19}$, —OCH(CH$_3$)C$_7$H$_{15}$, —OC$_{10}$H$_{21}$, —OCH(CH$_3$)C$_8$H$_{17}$, —OC$_{11}$H$_{23}$, —OCH(CH$_3$)C$_9$H$_{19}$, —OC$_{12}$H$_{24}$, —OCH(CH$_3$)C$_{10}$H$_{21}$, —(CH$_2$)$_2$—O—CH$_3$, —(CH$_2$)$_3$—O—CH$_3$, —(CH$_2$)$_3$—O—C$_2$H$_5$, —(CH$_2$)$_4$—O—C$_2$H$_5$, —(CH$_2$)$_5$—O—C$_2$H$_5$, —(CH$_2$)$_6$—O—CH$_3$, —(CH$_2$)$_2$CH═CH$_2$, —(CH$_2$)$_3$CH═CH$_2$, —(CH$_2$)$_4$—CH═CH$_2$, —(CH$_2$)$_5$CH═CH$_2$, —(CH$_2$)$_7$CH═CH$_2$, —O(CH$_2$)$_3$CH═CH$_2$, —O(CH$_2$)$_4$—CH═CH$_2$, —O(CH$_2$)$_5$CH═CH$_2$, —O(CH$_2$)$_7$CH═CH$_2$, —SC$_4$H$_9$, —SC$_5$H$_{11}$, —SCH(CH$_3$)C$_3$H$_7$, —SC$_6$H$_{13}$, —SCH(CH$_3$)C$_4$H$_9$, —SC$_7$H$_{15}$, —SCH(CH$_3$)C$_5$H$_{11}$, —SC$_8$H$_{17}$, —SCH(CH$_3$)C$_6$H$_{13}$, —SC$_9$H$_{19}$, —SCH(CH$_3$)C$_7$H$_{15}$, —SC$_{10}$H$_{21}$, —SCH(CH$_3$)C$_8$H$_{17}$, —SC$_{11}$H$_{23}$, —SCH(CH$_3$)C$_9$H$_{19}$, —SC$_{12}$H$_{24}$, —SCH(CH$_3$)C$_{10}$H$_{21}$, —(CH$_2$)$_2$—S—CH$_3$, —(CH$_2$)$_2$—S—C$_2$H$_5$, —(CH$_2$)$_3$—S—CH$_3$, —(CH$_2$)$_3$—S—C$_2$H$_5$, —(CH$_2$)$_4$—S—C$_2$H$_5$, —(CH$_2$)$_5$—S—C$_2$H$_5$, —(CH$_2$)$_6$—S—CH$_3$, —(CH$_2$)$_3$CF$_2$CF$_3$, —(CH$_2$)$_3$(CF$_2$)$_2$CF$_3$, —CH$_2$CHF(CH$_2$)$_3$CH$_3$, —(CH$_2$)$_3$(CF$_2$)$_3$CF$_3$, —CH$_2$CHF(CH$_2$)$_4$—CH$_3$, —(CH$_2$)$_3$(CF$_2$)$_4$CF$_3$, —CH$_2$CHF(CH$_2$)$_5$CH$_3$, —(CH$_2$)$_3$(CF$_2$)$_5$CF$_3$, —CH$_2$CHF(CH$_2$)$_6$CH$_3$, —(CH$_2$)$_3$(CF$_2$)$_6$CF$_3$, —CH$_2$CHF(CH$_2$)$_7$CH$_3$, —O(CH$_2$)$_3$CF$_2$CF$_3$, —O(CH$_2$)$_3$(CF$_2$)$_2$CF$_3$, —OCH$_2$CHF(CH$_2$)$_3$CH$_3$, —O(CH$_2$)$_3$(CF$_2$)$_3$CF$_3$, —OCH₂CHF(CH₂)₄CH₃, —O(CH₂)₃(CF₂)₄CF₃,
—OCH₂CHF(CH₂)₅CH₃, —O(CH₂)₃(CF₂)₅CF₃,
—OCH₂CHF(CH₂)₆CH₃, —O(CH₂)₃(CF₂)₆CF₃, and
—OCH₂CHF(CH₂)₇CH₃.

More preferably, R is, for instance, —C₅H₁₁, —C₆H₁₃, —C₇H₁₅, —C₈H₁₇, —C₉H₁₉, —C₁₀H₂₁, —OC₄H₉, —OC₅H₁₁, —OCH(CH₃)C₃H₇, —OC₆H₁₃, —OCH(CH₃)C₄H₉, —OC₇H₁₅, —OCH(CH₃)C₅H₁₁, —OC₈H₁₇, —OCH(CH₃)C₆H₁₃, —OC₉H₁₉, —OCH(CH₃)C₇H₁₅, —OC₁₀H₂₁, —SC₄H₉, —SC₅H₁₁, —SCH(CH₃)C₃H₇, —SC₆H₁₃, —SCH(CH₃)C₄H₉, —SC₇H₁₅, —SCH(CH₃)C₅H₁₁, —SC₈H₁₇, —SCH(CH₃)C₆H₁₃, —SC₉H₁₉, —SCH(CH₃)C₇H₁₅, —SC₁₀H₂₁, —SCH(CH₃)C₈H₁₇, —(CH₂)₃CF₂CF₃, —(CH₂)₃(CF₂)₂CF₃, —(CH₂)₃(CF₂)₃CF₃, —(CH₂)₃(CF₂)₄F₃, —(CH₂)₃(CF₂)₅CF₃, —(CH₂)₃(CF₂)₆CF₃, —O(CH₂)₃CF₂CF₃, —O(CH₂)₃(CF₂)₂CF₃, —OCH₂CHF(CH₂)₃CH₃, —O(CH₂)₃(CF₂)₃CF₃, —OCH₂CHF(CH₂)₄CH₃, —O(CH₂)₃(CF₂)₄CF₃, —OCH₂CHF(CH₂)₅CH₃, —O(CH₂)₃(CF₂)₅CF₃, —OCH₂CHF(CH₂)₆CH₃, —O(CH₂)₃(CF₂)₆CF₃, and —OCH₂CHF(CH₂)₇CH₃.

Most preferably, R is, for instance, —C₅H₁₁, —C₆H₁₃, —C₇H₁₅, —C₈H₁₇, —C₉H₁₉, —C₁₀H₂₁, —OC₄H₉, —OC₅H₁₁, —OCH(CH₃)C₃H₇, —OC₆H₁₃, —OCH(CH₃)C₄H₉, —OC₇H₁₅, —OCH(CH₃)C₅H₁₁, —OC₈H₁₇, —OCH(CH₃)C₆H₁₃, —OC₉H₁₉, —OC₁₀H₂₁, —SC₄H₉, —SC₅H₁₁, —SCH(CH₃)C₃H₇, —SC₆H₁₃, —SCH(CH₃)C₄H₉, —SC₇H₁₅, —SCH(CH₃)C₅H₁₁, —SC₈H₁₇, —SCH(CH₃)C₆H₁₃, —SC₉H₁₉, —SC₁₀H₂₁, and —SCH(CH₃)C₈H₁₇.

A is independently 1,4-phenylene in which any hydrogen is replaced by fluorine.

Examples of "1,4-phenylene in which any hydrogen is replaced by fluorine" include, for instance, the rings (5-1) to (5-9) below, preferably the rings (5-3) to (5-9), more preferably, the rings (5-4), (5-5), (5-7) to (5-9), and most preferably, the ring (5-9).

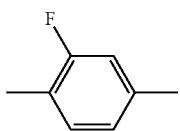
(5-1)

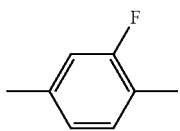
(5-2)

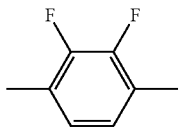
(5-3)

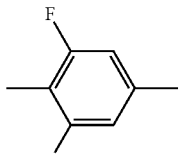
(5-4)

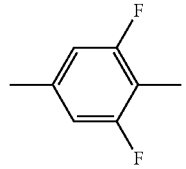
(5-5)

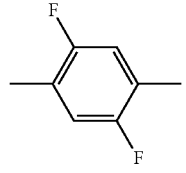
(5-6)

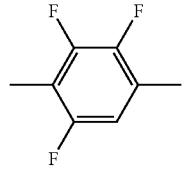
(5-7)

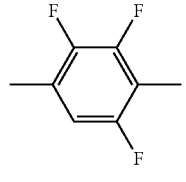
(5-8)

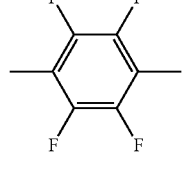
(5-9)

Z is independently a single bond, —(CH₂)₂—, —COO—, —OCO—, —CONH—, —NHCO—, —CH₂O—, —OCH₂—, —CF₂O—, —OCF₂—, —CH=CH—, —C≡C—, —CF=CF—, —CH₂CO—, —COCH₂—, —(CH₂)₄—, —(CH₂)₃—O—, —O—(CH₂)₃—, —(CH₂)₂COO—, —OCO(CH₂)₂—, —(CH₂)₂CONH—, —NHCO(CH₂)₂—, —CH=CH(CH₂)₂—, —(CH₂)₂CH=CH—, —(CH₂)₂CF₂O—, or —OCF₂(CH₂)₂—.

The conformation of bonding groups having double bonds such as —CH=CH— is preferably trans, rather than cis.

Preferable examples of Z include a single bond, —(CH₂)₂—, —COO—, —OCO—, —CONH—, —NHCO—, —CH₂O—, —OCH₂—, —CH=CH—, —C≡C—, —(CH₂)₄—, —(CH₂)₃—O—, —O—(CH₂)₃—, —(CH₂)₂COO—, —OCO(CH₂)₂—, —(CH₂)₂CONH—, —NHCO(CH₂)₂—, —CH=CH(CH₂)₂—, and —(CH₂)₂CH=CH—.

More preferable examples of Z include a single bond, —(CH₂)₂—, —COO—, —CONH—, —CH₂O—, —CH=CH—, —C≡C—, —(CH₂)₄—, —(CH₂)₃O—, —(CH₂)₂COO—, and —(CH₂)₂CONH—.

Most preferable examples of Z include a single bond, —(CH₂)₂—, —COO—, —CH=CH—, and —C≡C—.

n is independently an integer from 1 to 3. Since it does not make a substantial difference to the characteristics of the material, the material (1) may comprise isotopes such as 2H (heavy hydrogen), ¹³C or the like, in amounts larger than their natural abundance.

[5] The organic semiconductor material in [4], wherein in formula (1), R is hydrogen, a C1 to C20 linear or branched alkyl, C1 to C20 linear or branched alkoxy, C2 to C20 linear or branched alkenyl, C2 to C20 linear or branched alkynyl, C2 to C20 linear or branched alkoxyalkyl, C1 to C20 linear or branched alkenyloxy, C1 to C20 linear or branched thioalkyl, or C2 to C20 linear or branched thioalkenyl, and any hydrogen in these groups may be replaced by fluorine;

A is independently 2-fluoro-1,4-phenylene, 2,3-difluoro-1,4-phenylene, 2,6-difluoro-1,4-phenylene, 2,3,5-trifluoro-1,4-phenylene, or 2,3,5,6-tetrafluoro-1,4-phenylene;

and Z is independently a single bond, —(CH$_2$)$_2$—, —COO—, —OCO—, —CONH—, —NHCO—, —CH$_2$O—, —OCH$_2$—, —CH=CH—, —C≡C—, —CF=CF—, —(CH$_2$)$_2$COO—, —OCO(CH$_2$)$_2$—, —(CH$_2$)$_2$CONH—, —NHCO(CH$_2$)$_2$—, —CH=CH(CH$_2$)$_2$—, or —(CH$_2$)$_2$CH=CH—.

[6] The organic semiconductor material in [4], comprising at least one compound selected from the group of compounds represented by formula (2):

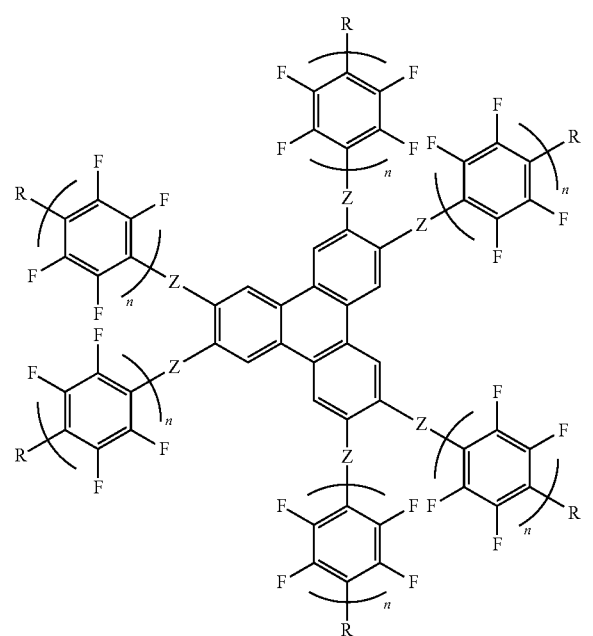

(2)

in formula (2), R is a C1 to C24 linear or branched alkyl, C1 to C23 linear or branched alkoxy, C2 to C24 linear or branched alkenyl, C2 to C24 linear or branched alkynyl, C2 to C23 linear or branched alkoxyalkyl, C2 to C23 linear or branched alkenyloxy, C1 to C20 linear or branched thioalkyl, or C2 to C23 linear or branched thioalkenyl, and any hydrogen in these groups may be replaced by fluorine;

Z is independently a single bond, —(CH$_2$)$_2$—, —COO—, —OCO—, —CONH—, —NHCO—, —CH$_2$O—, —OCH$_2$—, —CH=CH—, —C≡C—, —CF=CF—, —(CH$_2$)$_2$COO—, —OCO(CH$_2$)$_2$—, —(CH$_2$)$_2$CONH—, —NHCO(CH$_2$)$_2$—, —CH=CH(CH$_2$)$_2$—, or —(CH$_2$)$_2$CH=CH—;

and n is independently 1 or 2.

[7] The organic semiconductor material in [4], comprising at least one compound selected from the group of compounds represented by formula (3):

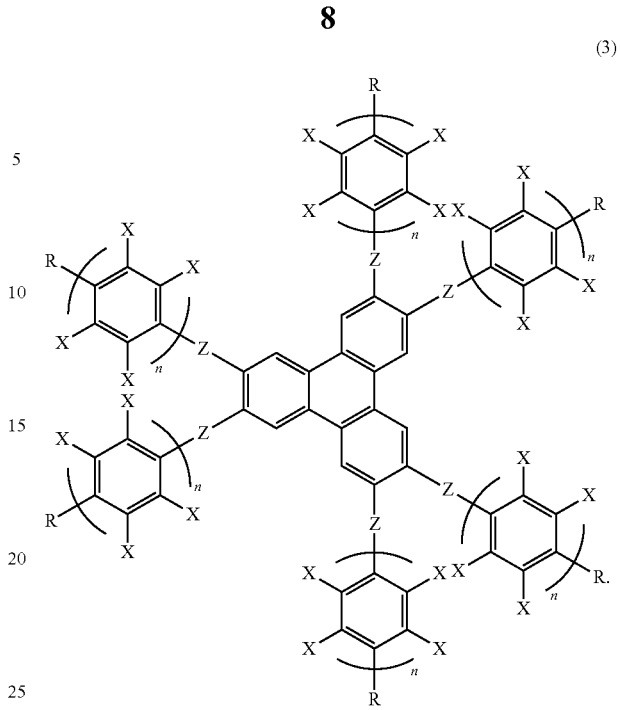

(3)

in formula (3), R is a C1 to C24 linear or branched alkyl, C1 to C23 linear or branched alkoxy, C2 to C24 linear or branched alkenyl, C2 to C24 linear or branched alkynyl, C2 to C23 linear or branched alkoxyalkyl, C2 to C23 linear or branched alkenyloxy, C1 to C20 linear or branched thioalkyl, or C2 to C23 linear or branched thioalkenyl, and any hydrogen in these groups may be replaced by fluorine;

Z is independently a single bond, —(CH$_2$)$_2$—, —COO—, —OCO—, —CONH—, —NHCO—, —CH$_2$O—, —OCH$_2$—, —CH=CH—, —C≡C—, —CF=CF—, —(CH$_2$)$_2$COO—, —OCO(CH$_2$)$_2$—, —(CH$_2$)$_2$CONH—, —NHCO(CH$_2$)$_2$—, —CH=CH(CH$_2$)$_2$—, or —(CH$_2$)$_2$CH=CH—;

X is independently hydrogen or fluorine but not all X are hydrogen or fluorine; and n is independently 1 or 2.

[8] At least one compound selected from the group of compounds represented by formula (4):

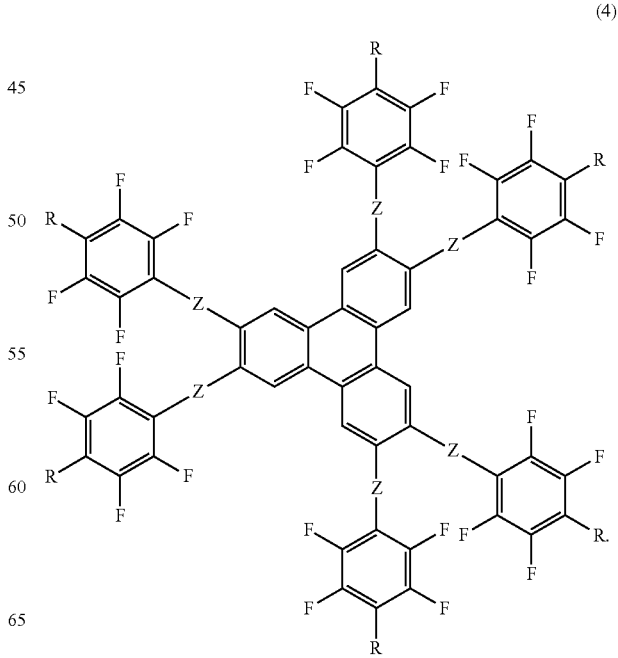

(4)

in formula (4), R is independently a C1 to C20 linear or branched alkyl, C1 to C20 linear or branched alkoxy, C2 to C20 linear or branched alkenyl, C2 to C20 linear or branched alkynyl, C2 to C20 linear or branched alkoxyalkyl, C2 to C20 linear or branched alkenyloxy, C1 to C20 linear or branched thioalkyl, or C2 to C20 linear or branched thioalkenyl;

and Z is independently a single bond, —(CH$_2$)$_2$—, —CONH—, —NHCO—, —CH$_2$O—, —OCH$_2$—, —CH=CH—, —C≡C—, —CF=CF—, —(CH$_2$)$_2$COO—, —OCO(CH$_2$)$_2$—, —(CH$_2$)$_2$CONH—, —NHCO(CH$_2$)$_2$—, —CH=CH(CH$_2$)$_2$— or —(CH$_2$)$_2$CH=CH—.

[9] At least one compound selected from the group of compounds represented by formula (5):

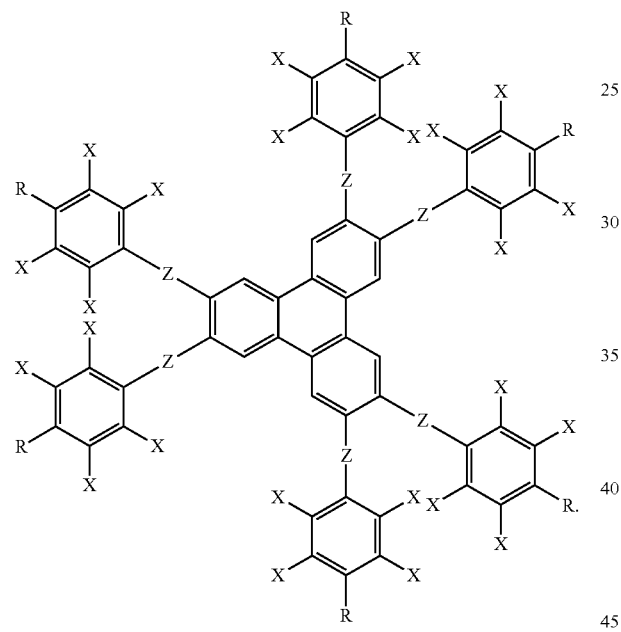

(5)

in formula (5), R is independently a C1 to C20 linear or branched alkyl, C1 to C20 linear or branched alkoxy, C2 to C20 linear or branched alkenyl, C2 to C20 linear or branched alkynyl, C2 to C20 linear or branched alkoxyalkyl, C2 to C20 linear or branched alkenyloxy, C1 to C20 linear or branched thioalkyl, or C2 to C20 linear or branched thioalkenyl;

Z is independently a single bond, —(CH$_2$)$_2$—, —CONH—, —NHCO—, —CH$_2$O—, —OCH$_2$—, —CH=CH—, —C≡C—, —CF=CF—, —(CH$_2$)$_2$COO—, —OCO(CH$_2$)$_2$—, —(CH$_2$)$_2$CONH—, —NHCO(CH$_2$)$_2$—, —CH=CH(CH$_2$)$_2$—, or —(CH$_2$)$_2$CH=CH—;

and X is independently hydrogen or fluorine but not all X are hydrogen or fluorine.

[10] At least one compound selected from the group of compounds represented by formula (6):

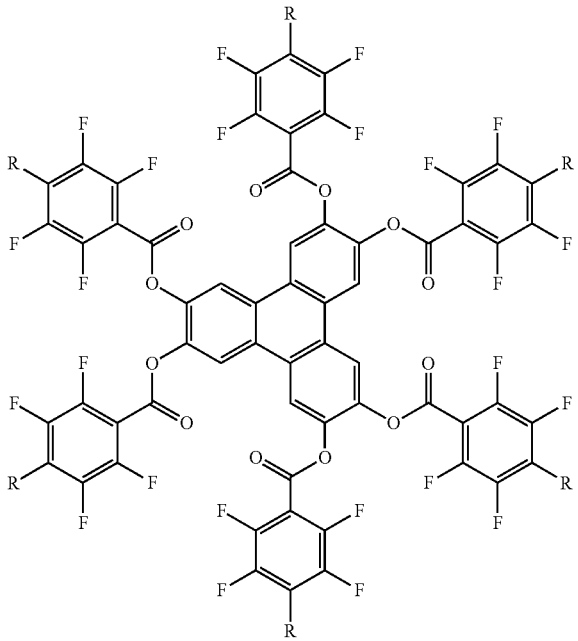

(6)

in formula (6), R is a C1 to C24 linear or branched alkyl, C1 to C7 linear alkoxy, C9 to C23 linear alkoxy, C$_1$ to C$_{23}$ branched alkoxy, C2 to C24 linear or branched alkenyl, or C1 to C23 linear or branched thioalkyl.

[11] At least one compound selected from the group of compounds represented by formula (7):

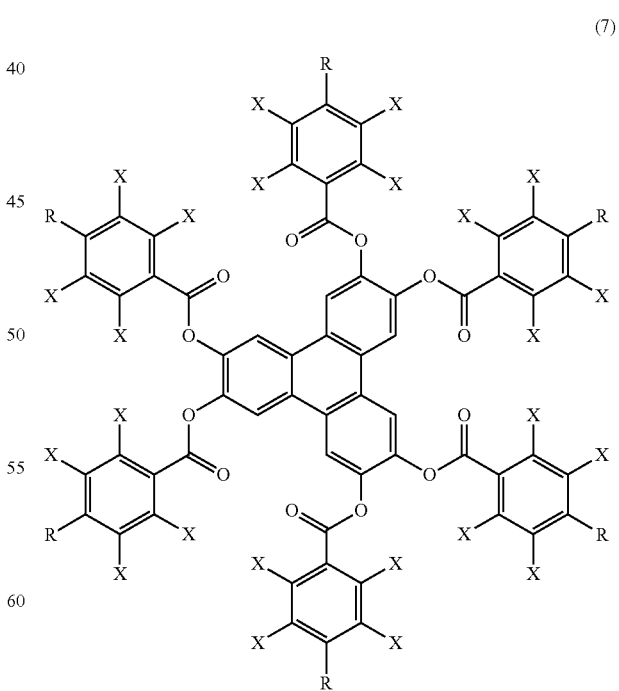

(7)

in formula (7), R is a C1 to C24 linear or branched alkyl, C1 to C9 linear alkoxy, C11 to C23 linear alkoxy, C1 to C23 branched alkoxy, C2 to C24 linear or branched alkenyl, or C1 to C23 linear or branched thioalkyl;

and X is independently hydrogen or fluorine but not all X are hydrogen or fluorine.

[12] A composition containing the organic semiconductor material in any one of [1] to [7], or the compound in any one of [8] to [11].

[13] An organic semiconductor thin film comprising the organic semiconductor material in any one of [1] to [7], the compound in any one of [8] to [11], or the composition in [12].

[14] An organic semiconductor element comprising the organic semiconductor thin film in [13] and a plurality of electrodes.

[15] A transistor comprising a gate electrode, a dielectric layer, a source electrode, a drain electrode and a semiconductor layer, wherein the semiconductor layer comprises the organic semiconductor thin film in [13].

The present invention allows increasing the temperature stability, and expanding the temperature range, of a columnar phase in which columns obtained by accumulating in a stack a liquid crystalline compound having substituents on the periphery of a rigid plate-like central structure a realigned in the shape of a hexagonal crystal, thereby providing an organic semiconductor material that enables efficient charge transport under a wider range of conditions.

BRIEF DESCRIPTION OF THE DRAWINGS

FIG. 1 is a diagram illustrating schematically a cell.

DESCRIPTION OF THE PREFERRED EMBODIMENTS

The terms used in the present specification are as follows. The "at least one compound selected from the group of compounds represented by formula (1)" is abbreviated as "compound (1)". "Compound (1)" means one compound or two or more compounds represented by formula (1). The same applies to the compounds represented by other formulas. The organic semiconductor material comprising at least one compound selected from the group of compounds represented by formula (1) will be referred to as "organic semiconductor material (1)" or "material (1)" for short.

The organic semiconductor material (1) of the present invention is explained in more detail first. The phase transition temperature and the temperature range of the liquid crystal phase in the material (1) can be adjusted by suitably selecting the terminal groups, ring structure, and bonding groups of the material (1). As a result, this allows adjusting arbitrarily charge mobility and the temperature range in which charge transfer is possible, in the organic semiconductor material. The effects that the terminal groups R, rings A and bonding groups Z impart to the characteristics of the material (1) are explained next.

When R is linear, the temperature range of the liquid crystal phase is broad. When R is branched, the clearing point is lowered, and, in a composition, compatibility improves vis-à-vis other liquid crystal organic semiconductor materials. When R has optical activity, moreover, a helical period can form inside the columns.

When the ring A is 3,5-tetrafluoro-1,4-phenylene, of 2,3, 5,6-tetrafluoro-1,4-phenylene the temperature range of the $Col_h$ phase is broad, and the clearing point thereof is high.

When the bonding group Z is a single bond, —(CH$_2$)$_2$—, —COO—, —OCO—, —CH$_2$O—, —OCH$_2$—, —CF$_{2O}$—, —OCF$_2$—, —CH$_2$CO—, or —COCH$_2$, the clearing point is high, and yet higher when Z is —CONH—, —NHCO—, —CH=CH—, —C≡C—, or —CF=CF—. When the bonding group Z is —(CH$_2$)$_4$—, —(CH$_2$)$_3$—O—, —O—(CH$_2$)$_3$—, —(CH$_2$)$_2$COO—, —OCO(CH$_2$)$_2$—, —(CH$_2$)$_2$CONH—, —NHCO(CH$_2$)$_2$—, —CH=CH(CH$_2$)$_2$—, —(CH$_2$)$_2$CH=CH—, —(CH$_2$)$_2$CF$_2$O—, or —OCF$_2$(CH$_2$)$_2$— the clearing point can be adjusted to be lower.

The clearing point becomes higher as the number n increases from 1 to 3. By suitably selecting the terminal groups, the rings and the bonding groups, as described above, it becomes thus possible to obtain a material having the envisaged characteristics.

The compound of the present invention, which is accumulated in a stack to form columns aligned hexagonally, in particular, to form a $Col_h$ phase, is most preferably used as an organic semiconductor material. Upon application in an actual organic semiconductor device, however, the organic semiconductor material must exhibit a hexagonal crystal alignment over a wide temperature range. The organic semiconductor material of the present invention, wherein columns are aligned hexagonally over a wide temperature range, is an excellent material in such terms.

In the present specification, "columns of an accumulated stack are aligned in the shape of a hexagonal crystal" means that columns in which the liquid crystalline compound having substituents in the periphery of a rigid plate-like central structure is accumulated in a stack are aligned in the shape of a hexagonal crystal, and applies not only to a liquid crystal but also to a mesophase, a glass solid phase, and a crystalline solid phase. Herein, the liquid crystal is preferably a discotic liquid crystal.

A discotic liquid crystal is a liquid crystal phase formed by molecules spread over a plane and which adopts ordinarily a structure where various side chains are bonded to a core having a ring-like structure. The core structures include, for instance, benzene, triphenylene, porphyrin, phthalocyanine, and cyclohexane structures. In the present invention a material or a compound is used. The compound can be used singly or in mixtures of two or more.

Besides the above material, other additives may also be formulated, as the case may require, for instance antioxidants, light stabilizers, leveling agents, surfactants, preservatives, lubricants, solvents, aging inhibitors, wettability-improving materials and the like.

In the organic semiconductor material, high-speed charge transfer in the $Col_h$ phase is preferably parallel to the direction along the column axes, i.e. parallel to the orientation axis of the disc-shaped molecules, while the electrodes are preferably perpendicular to the orientation axis of the disc-shaped molecules. The perpendicular direction varies herein by ±45 degrees relative to the vertical.

The material or compound can be coated or printed on a substrate by heating and melting the material of the present invention into a molten liquid. When such a molten liquid is used, the material can be sealed into a narrowly-spaced cell by capillarity. A printing method can also be employed wherein the molten liquid is dripped using a nozzle. On the other hand, an organic semiconductor thick film having an arbitrary thickness can be manufactured by using this molten liquid made into a paste.

Various organic solvents can be used as organic solvents capable of dissolving the material of the present invention. Organic solvents that can be used include, for instance, pentane, hexane, diethyl ether, t-butyl methyl ether, tetrahydrofuran, methanol, ethanol, 2-propanol, ethyl acetate, ethyl lactate, dioxane, benzene, toluene, xylene, dichloromethane, chloroform, acetonitrile, acetone, cyclohexane, cyclopentane, cyclohexanone, γ-butyrolactone, butyl cellosolve, N-methyl-2-pyrrolidone, dimethylformamide, dimethyl sulfoxide, water, and mixtures of the foregoing.

The material of the present invention is very readily dissolved in the above organic solvents, and hence can be obtained in high-concentration solutions. Accordingly, an organic semiconductor thin film can be prepared by coating or printing such a solution onto a substrate. The thickness of the organic semiconductor thin film used in an organic semiconductor element ranges ordinarily from 10 to 1000 nanometers, and the concentration of the material in the solution from 0.1 to 10 wt %. Upon manufacture of an organic semiconductor thin film having a thickness in excess of 1,000 nanometers, the molten material is preferably used without modification.

Various substrates can be used herein as the substrate onto which the material of the present invention and the solution thereof can be coated or printed. Examples of substrates that can be used include, for instance, glass substrates, metallic substrates of gold, copper, silver or the like, crystalline silicon substrates, amorphous silicon substrates, triacetyl cellulose substrates, norbornene substrates, polyethylene terephthalate substrates, polyester substrates, polyvinyl substrates, polypropylene substrates, polyethylene substrates and the like.

Various methods can be used for coating the material of the present invention and a solution thereof, for instance spin coating, dip coating, blade coating and the like.

Also, various methods can be used for printing the material of the present invention and a solution thereof, for instance screen printing, ink jet printing, planographic printing, gravure printing, relief printing and the like. Among these, ink jet printing by a printer, using a solution of the unmodified material as ink, is preferable on account of the simplicity of the method.

The material of the present invention has an appropriately low clearing point and high solubility in organic solvents, and hence can be used in undemanding manufacturing processes such as casting or printing. It is therefore possible to manufacture organic semiconductor thin films or organic semiconductor elements without the material losing its intrinsic charge mobility.

Ordinary manufacturing methods of the material (1) of the present invention are explained next. The material (1) can be manufactured by suitably selecting and combining methods described in "Courses in Experimental Chemistry" (Maruzen), Fourth Edition, Organic Synthesis, John Wiley & Sons, Inc, Organic Reactions, John Wiley & Sons, Inc, or other literature sources. The following rings can be synthesized using the methods described in the respective cited documents: triphenylene rings using the method described in (N. Herbert, et al, Synthesis, 1994, 5, 477); coronene rings using the method described in (P. M. Donovan et al, Journal of the American Chemical Society, 2004, 126(10), 3108); benzocoronene using the method described in (B, Alameddine et al, Chemistry of Materials, 2005, 17(19), 4798); phthalocyanine rings using the method described in (L. Pui-Chi et al, Synthesis, 2005, 7, 1141); porphyrin rings using the method described in (S. Neya et al, Journal of Heterocyclic Chemistry, 1993, 30(2), 549); truxene rings using the method described in (K. Jacob et al, Europian Journal of Organic Chemistry, 2000, 11, 2047); pyran rings using the method described in (G, Mihai et al, Anorganische Chemie Organische Chemie, 1986, 41B(4), 502); tricycloquinazoline rings using the method described in (E, Keinan et al, DE4340408); phenyl acetylene rings using the method described in (K. Kobayashi et al, Journal of Organic Chemistry, 2004, 69(7), 2487); calixarene rings using the method described in (C. D. Gutsche et al, Journal of Organic Chemistry, 1986, 51(5), 742); pyrene rings using the method described in (M. Tashiro et al, Journal of Organic Chemistry, 1987, 52(15), 3196); perylene rings using the method described in (M. Philippe et al, Synthesis, 1988, 11, 894); oligothiophene rings using the method described in (A. Tabet et al, Organic Letters, 2003, 5(11), 1817); decacyclene rings using the method described in (B. Igrlesias et al, Synlett, 2002, 3, 486);

and rufigallol rings using the method described in (K. S. Raja et al, Chemistry Materials, 1997, 9, 1630). Examples of the synthesis of the bonding groups Z are described in sections (I) to (X). The synthesis schemes are explained first. In the schemes, $MSG^1$ and $MSG^2$ are organic chemical groups. Among thus, one is an organic chemical group comprising a triphenylene ring. The compounds (1-1) to (1-10) correspond to the material of the present invention.

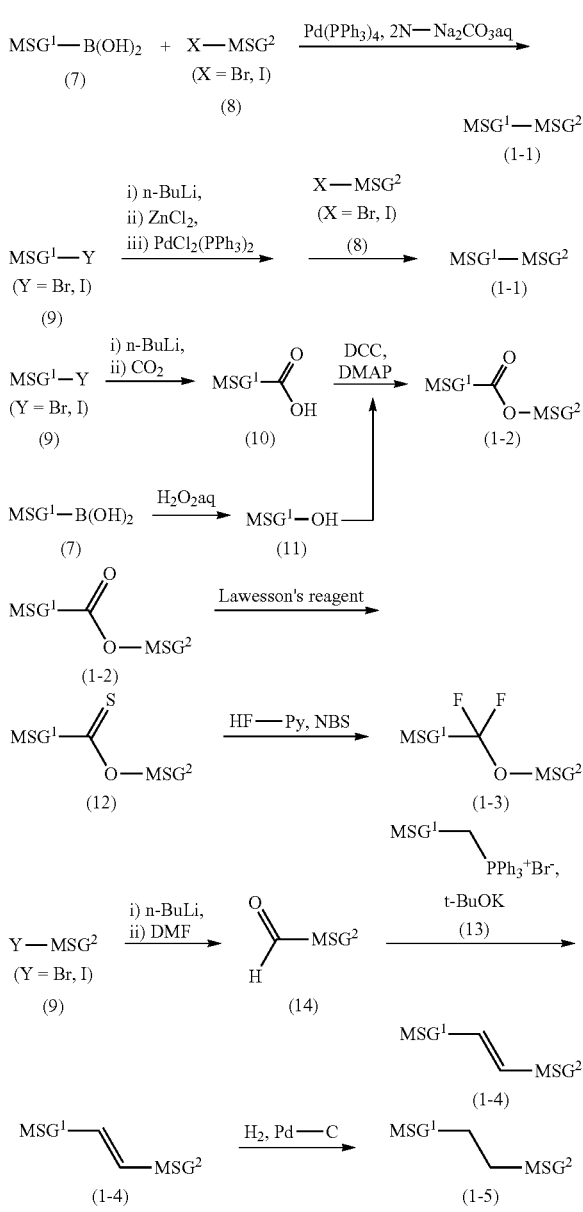

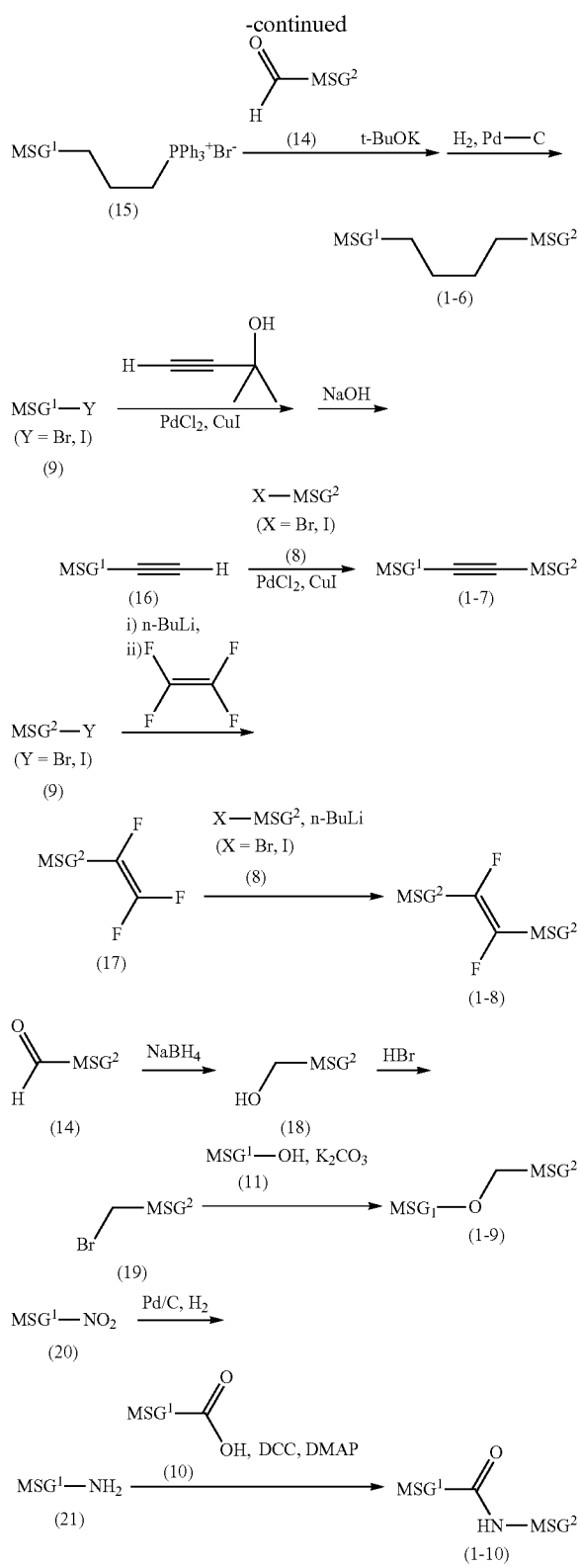

prepared by subjecting the compound (9), prepared by a known method, to the sequential action of catalysts such as n-butyllithium(n-BuLi), zinc chloride, dichlorobis(triphenylphosphine)palladium (PdCl$_2$ (PPh$_3$)$_2$), and the compound (8).

(II) Formation of —COO— and —OCO—

The carboxylic acid (10) is then obtained by forming a lithiation product of (9) through the reaction with butyl lithium, followed by a reaction with carbon dioxide. The material (1-2) having —COO— is prepared through dehydration condensation of the compound (10) and an alcohol (11) or phenol (12) prepared by a known method. A material having —OCO— can also be prepared in accordance with this method.

(III) Formation of —CF$_2$O— and —OCF$_2$—

The material (1-2) is treated with a sulfurating agent such as Lawesson's reagent to yield the compound (12). This compound is fluorinated with a hydrogen fluoride-pyridine complex (M. Kuroboshi et al., Chem. Lett., 1992, 827) or with (diethylamino)sulfur trifluoride (William H. Bunnelle et al., J. Org. Chem. 1990, 55, 768), to yield a material (1-3) having —CF$_2$O—. A compound having —OCF$_2$— can also be prepared in accordance with this method.

(IV) Formation of —CH=CH—

The compound (13) prepared by a known method is reacted with a base such as potassium t-butoxide (t-BuOK) to yield a phosphorus ylide. Meanwhile, after formation of a lithiation product through reaction with butyllithium, the compound (9) is reacted with a formamide such as N,N-dimethylformamide to give an aldehyde (14). This aldehyde (14) is reacted with the phosphorus ylide to give the material (1-4). Since the reaction may yield a cis isomer, depending on the reaction conditions, the material is isomerized into a trans isomer in accordance with a known method.

(V) Formation of —(CH$_2$)$_2$—

The material (1-5) is prepared by catalytic hydrogenation of the material (1-4) in the presence of a catalyst such as palladium carbon (Pd—C).

(VI) Formation of —(CH$_2$)$_4$—

Using the compound (15) instead of the compound (13), —CH=CH— is formed in accordance with the method (IV), followed by catalytic hydrogenation to prepare the material (1-6)

(VII) Formation of —C≡C—

The compound (9) is reacted with 2-methyl-3-butyn-2-ol in the presence of catalysts of palladium dichloride and a copper halide, followed by deprotection under basic conditions, to give the compound (16). The material (1-7) is prepared by the reaction of the compound (16) with the compound (8) in the presence of catalysts of palladium dichloride and a copper halide.

(VIII) Formation of —CF=CF—

After formation of a lithiation product through reaction with butyllithium, the compound (9) is reacted with tetrafluoroethylene to give the compound (17). The material (1-8) is prepared by reacting the lithiation product derived from compound (8) using n-butyllithium, and the compound (17).

(IX) Formation of —CH$_2$O— or —OCH$_2$—

The compound (14) is treated with a reducing agent such as sodium borohydride (NaBH$_4$), to yield the compound (18). The compound (18) is reacted with a halogenating agent such as hydrobromic acid to yield the compound (19). The compounds (19) and (11) are reacted in the presence of potassium carbonate or the like to prepare the material (1-9).

(X) Formation of —CONH— or —NHCO—

An amine (21) is obtained through reduction of the nitro compound (20) by means of catalytic hydrogenation or the (I) Formation of a Single Bond The material (1-1) is prepared by the reaction of an arylboronic acid derivative (7) with the compound (8), prepared using a known method, in the presence of an aqueous solution of carbonate and a catalyst such as tetrakis(triphenylphosphine)palladium (Pd(PPh$_3$)$_4$). The material (1-1) can also be like. The amine (20) and the compound (10) are dehydration-condensed to prepare the material (1-10).

An organic semiconductor thin film and an organic semiconductor element that can be manufactured using the material of the present invention are explained next.

For manufacturing an organic semiconductor element, preferably, a pattern is formed through printing, such printing using preferably a high-concentration solution or molten liquid of the material of the present invention. A high-concentration solution or molten liquid are advantageous in that they allow using ink jet printing, mask printing, screen printing and offset printing. During the manufacture of the organic semiconductor element through printing, the material of the present invention contributes to enhancing circuit purity, manufacturing efficiency, as well as to reducing the cost and weight of the element. Since, as explained above, the material of the invention can be manufactured in a continuous operation that requires no heating or vacuum processes, the invention contributes to lowering costs and to increase responsiveness towards process changes. The material (1), which is extremely soluble inorganic solvents, has excellent characteristics in such terms.

The material of the present invention can be used as a resin composition (blended resin) in combination with a synthetic organic polymer. The content of the compound of the present invention in such a blended resin ranges from 1 wt % to 99 wt %, preferably from 10 wt % to 99 wt %, and more preferably from 50 wt % to 99 wt %.

The above synthetic organic polymers may be thermoplastic polymers, thermosetting polymers, engineering plastics and electroconductive polymers. Specific examples thereof include polyesters, polyimides, polystyrene, polymethacrylic acid, polyacrylic acid, polyethylene, polypropylene, polycylcoolefins, polyvinyl chloride, polyvinylidene chloride, polyvinyl acetate, polycarbonate, phenolic resins, polyurethane resins, epoxy resins, melamine resins, polytetrafluoroethylene resins, polyacetylene, polypyrroles, polyarylene-vinylene and the like.

A rectifying element, a current driving transistor or an element such as a thyristor/triac/diac or the like for switching can be built by using the organic semiconductor thin film of the present invention as a constituent element, and/or as an element having current rectifying or signal processing functions, in combination with other organic or inorganic materials having semiconductor properties. The organic semiconductor thin film of the present invention can also be used as a display element, and is particularly useful as a display element where all the members are made of organic compounds. The organic semiconductor thin film of the present invention can be used, for instance, in liquid crystal display elements, electronic paper and the like. Specifically, flexible sheet-like display devices or devices responsive to unique identification codes such as electronic paper, IC cards or the like can be manufactured by forming the semiconductor thin film of the present invention, together with one or more layers containing a constituent element that imparts functionality to the thin film, onto an insulating substrate made of a pliable polymer.

Flexible display elements can be provided by using a display element in which the organic semiconductor thin film of the present invention is formed on a pliable polymer substrate. This pliability allows realizing a display element that can be carried inside garment pockets, wallets and the like.

Devices responsive to unique identification codes are devices that react to electromagnetic waves having a specific wavelength or specific code, and which respond with an electromagnetic wave comprising a unique identification code. Device responsive to unique identification codes are used as a means for high-probability identification of people and/or documents in, for instance, re-usable passenger tickets or membership certificates, means for settling charges, identification seals for baggage or merchandise, allotment of labels or stamps, in business or administrative services and the like.

A device responsive to unique identification codes comprises a glass substrate or a substrate of a pliable polymer, upon which there a provided an antenna in tune with signals, for receiving the latter, and a semiconductor element operated with reception power, for responding with an identification signal.

The organic semiconductor element of the present invention can be used as a power amplifier element and/or a signal control element, a concrete example thereof being, for instance, a field effect transistor (FET) having a cross-sectional structure. To manufacture a FET, firstly a glass substrate and a drain electrode are formed. If necessary, an insulating layer may also be laminated. Thereon is then formed an organic semiconductor thin film through printing, coating or dripping of a solution or a molten liquid of the material (1), followed by formation of an insulating layer, as the case may require. Thereon may also be formed a gate electrode.

Such a FET can be used as liquid crystal display element or an EL element. Electron field-effect mobility can be determined from drain electrode/gate electrode curves by preparing a FET measurement cell comprising a thin film of the material (1) and by measuring current/voltage curves between the source-drain electrodes while modifying the gate electrode. Further, the on/off operation of the drain electrode can be observed based on the gate electrode.

The invention is explained in more detail below on the basis of examples, although it is in no way meant to be limited to or by them.

Measurement Method

The phase transition temperature was measured using a differential scanning calorimeter (DSC: 2920 MDSC), by TA-Instrument, at a rate of 5° C./minute. Phase identification was carried out by placing a sample on a polarization microscope (Olympus BH-2) equipped with a thermocontrolller (Mettler, FP80HT), with heating at a rate of 1° C./minute. The phase changes in the specimen were determined by observation of the optical texture. The $^1$H-NMR was measured using a 500 MHz nuclear magnetic resonance spectrometer (JNM-ECA500, by JEOL).

Measurement Method

Crystal is denoted as Cry. When crystals are distinguishable, they are denoted respectively as $Cry_1$ or $Cry_2$. A hexagonal columnar phase (hexagonal crystal prism-shaped phase) is denoted as $Col_h$. Liquid (isotropic) is denoted as Iso. The rectangular columnar phase (rectangular prism-shaped phase) is denoted as $D_r$. A tilted columnar phase is denoted as $D_t$. A discotic nematic phase is denoted as $N_D$. Uncharacterized phases are denoted as $X_1$, $X_2$, $X_3$ or $X_4$. Decomposition before formation of the isotropic liquid, or failed measurement of the isotropic liquid transition temperature, are denoted as Dec. In the notation of the phase transition temperature, "Cry 133 $Col_h$ 308 Iso" indicates that the transition temperature from crystal phase to hexagonal columnar phase is 133° C., and the transition temperature from hexagonal columnar phase to liquid is 308° C. The same applies to other notations.

EXAMPLE 1

Synthesis of 2,3,6,7,10,11-hexakis(4-butoxy-2,3,5,6-tetrafluorobenzoyloxy)triphenylene (A)

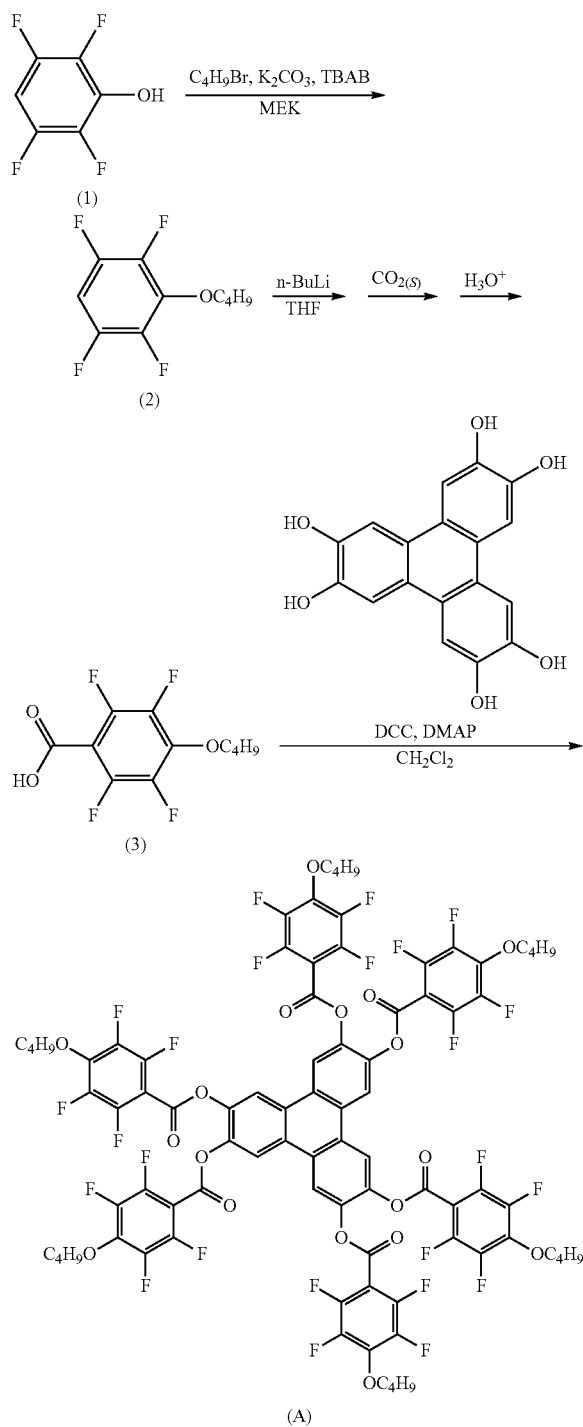

First Step

To 20.0 g of 2,3,5,6-tetrafluorophenol (1) dissolved in 100 mL of methyl ethyl ketone (MEK) there were added 18.3 g of potassium carbonate, 4.26 g of tetrabutylammonium bromide (TBAB) and 18.1 g of bromobutane dissolved in 50 mL of MEK, with heating under reflux for 4 hours. After cooling and addition of water, the organic layer was separated and the aqueous layer was extracted with diethyl ether. The organic layers were combined, were washed with saturated brine, and were then dried over anhydrous magnesium sulfate. The solvent was evaporated to yield 24.4 g (110 mmol) of 4-butoxy-2,3,5,6-tetrafluorobenzene (2).

Second Step 24.4 g of the compound (2) dissolved in 250 mL of tetrahydrofuran (THF) were cooled at −78° C. in an argon atmosphere; thereto were then dripped 82 mL of a 1.6 M/L n-butyllithium/hexane solution, with stirring for 2 hours at the same temperature. After addition of a suitable amount of crushed dry ice, the temperature was raised to room temperature, followed by stirring overnight. 200 mL of 3N hydrochloric acid were then added under ice cooling, the organic layer was separated, and the aqueous layer was extracted with diethyl ether. The organic layers were combined, were washed with saturated brine, and were then dried over anhydrous magnesium sulfate. After evaporating the solvent, the organic layer was recrystallized from hexane to yield 14.6 g (54.8 mmol) of 4-butoxy-2,3,5,6-tetrafluorobenzoic acid (3).

Third Step

A solution of 3.26 g of the compound (3), 0.44 g of 2,3,6,7,10,11-hexahydroxytriphenylene, and 1.50 g of 4-dimethylaminopyridine (DMAP) dissolved in 60 mL of dichloromethane was stirred at room temperature for 1 hour, then thereto was added, under ice cooling, 2.53 g of N,N-dicyclohexylcarbodiimide (DCC) dissolved in 20 mL of dichloromethane, followed by stirring under ice cooling for 5 minutes, and stirring overnight at room temperature. The precipitated dicyclohexylurea was filtered off, and the filtrate washed with 3-N hydrochloric acid, a saturated aqueous solution of sodium hydrogen carbonate, and saturated brine, followed by drying over anhydrous sodium sulfate. After evaporating the solvent, the product was purified by silica gel column chromatography and was recrystallized from hexane/ethanol to yield 2.10 g (1.15 mmol) of white solid 2,3,6,7,10,11-hexakis(4-butoxy-2,3,5,6-tetrafluorobenzoyloxy)triphenylene (A).

Phase transition temperature (° C.)

Cry 191 $X_1$ 232 $X_2$ 272 $X_3$ 311 $X_4$ 337 Iso $^1$H-NMR (CDCl$_3$: δ ppm)7.87(S,6H), 4.33(t, 12H), 1.82 (m, 12H), 1.57(m, 12H), 1.04(t, 18H).

EXAMPLE 2

Synthesis of 2,3,6,7,10,11-hexakis(4-hexyloxy-2,3,5,6-tetrafluorobenzoyl oxy)triphenylene (B)

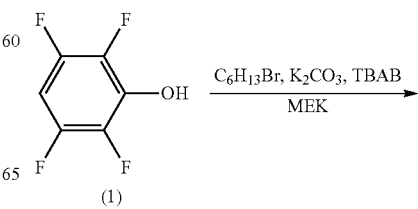

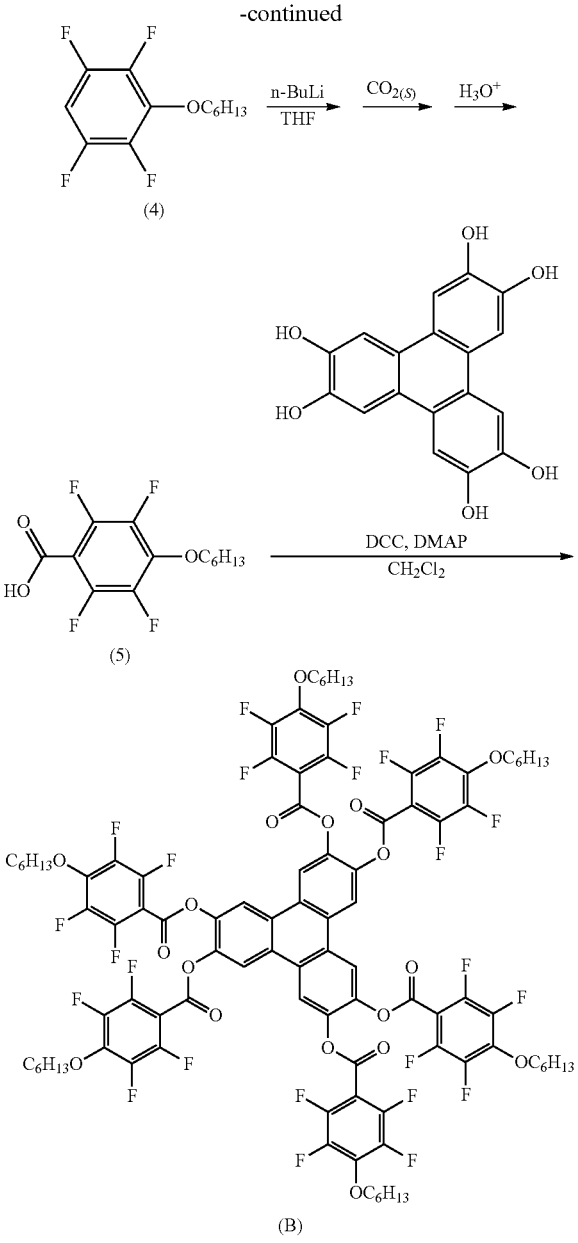

(4)

(5)

(B)

First Step

To 20.0 g of 2,3,5,6-tetrafluorophenol (1) dissolved in 100 mL of MEK there were added 18.3 g of potassium carbonate, 4.26 g of TBAB and 21.9 g of bromohexane dissolved in 50 mL of MEK, with heating under reflux for 4 hours. After cooling and addition of water, the organic layer was separated and the aqueous layer was extracted with diethyl ether. The organic layers were combined, were washed with saturated brine, and were then dried over anhydrous magnesium sulfate. The solvent was evaporated to yield 27.5 g (110 mmol) of 4-hexyloxy-2,3,5,6-tetrafluorobenzene (4).

Second Step 27.5 g of the compound (4) dissolved in 250 mL of THF were cooled at −78° C. in an argon atmosphere; thereto were then dripped 82 mL of a 1.6 M/L n-butyllithium/hexane solution, with stirring for 2 hours at the same temperature. After addition of a suitable amount of crushed dry ice, the temperature was raised to room temperature, followed by stirring overnight. 200 mL of 3N hydrochloric acid were then added under ice cooling, the organic layer was separated, and the aqueous layer was extracted with diethyl ether. The organic layers were combined, were washed with saturated brine, and were then dried over anhydrous magnesium sulfate. After evaporating the solvent, the organic layer was recrystallized from hexane to yield 25.9 g (88 mmol) of 4-hexyloxy-2,3,5,6-tetrafluorobenzoic acid (5).

Third Step

A solution of 2.35 g of the compound (5), 0.44 g of 2,3,6,7,10,11-hexahydroxytriphenylene, and 1.50 g of DMAP dissolved in 60 mL of dichloromethane was stirred at room temperature for 1 hour, then thereto was added, under ice cooling, 2.53 g of DCC dissolved in 20 mL of dichloromethane, followed by stirring under ice cooling for 5 minutes, and stirring overnight at room temperature. The precipitated dicyclohexylurea was filtered off, and the filtrate washed with 3-N hydrochloric acid, a saturated aqueous solution of sodium hydrogen carbonate, and saturated brine, followed by drying over anhydrous sodium sulfate. After evaporating the solvent, the product was purified by silica gel column chromatography and was recrystallized from hexane/ethanol to yield 1.40 g (0.71 mmol) of white solid 2,3,6,7,10,11-hexakis(4-hexyloxy-2,3,5,6-tetrafluorobenzoyl oxy)triphenylene (B).

Phase transition temperature (° C.): $Cry_1$ 130 $Cry_2$ 157 $Col_h$ 301 Iso

1H-NMR(CDCl$_3$: δ ppm) 7.97(S,6H), 4.34(t, 12H), 1.84 (m, 12H), 1.52(m, 12H), 1.41-1.38(m, 24H), 0.97(t, 18H).

EXAMPLE 3

Synthesis of 2,3,6,7,10,11-hexakis(4-heptyloxy-2,3,5,6-tetrafluorobenzoyloxy)triphenylene (C)

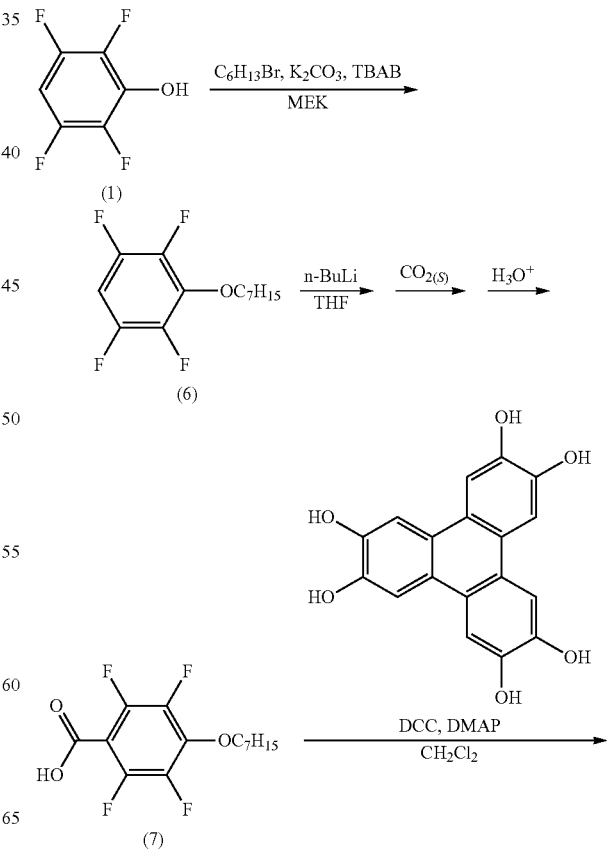

(1)

(6)

(7)

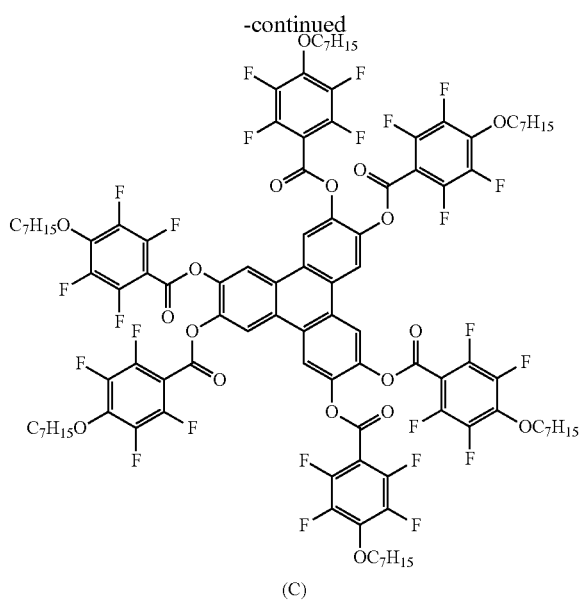

(C)

First Step

To 20.0 g of 2,3,5,6-tetrafluorophenol (1) dissolved in 100 mL of MEK there were added 18.3 g of potassium carbonate, 4.26 g of TBAB and 23.7 g of bromoheptane dissolved in 50 mL of MEK, with heating under reflux for 4 hours. After cooling and addition of water, the organic layer was separated and the aqueous layer was extracted with diethyl ether. The organic layers were combined, were washed with saturated brine, and were then dried over anhydrous magnesium sulfate. The solvent was evaporated to yield 31.8 g (120.4 mmol) of 4-heptyloxy-2,3,5,6-tetrafluorobenzene (6).

Second Step 31.8 g of the compound (6) dissolved in 250 mL of THF were cooled at −78° C. in an argon atmosphere; thereto were then dripped 93 mL of a 1.6 M/L n-butyllithium/hexane solution, with stirring for 2 hours at the same temperature. After addition of a suitable amount of crushed dry ice, the temperature was raised to room temperature, followed by stirring overnight. 200 mL of 3N hydrochloric acid were then added under ice cooling, the organic layer was separated, and the aqueous layer was extracted with diethyl ether. The organic layers were combined, were washed with saturated brine, and were then dried over anhydrous magnesium sulfate. After evaporating the solvent, the organic layer was recrystallized from hexane to yield 12.9 g (41 mmol) of 4-heptyloxy-2,3,5, 6-tetrafluorobenzoic acid (7).

Third Step

A solution of 7.76 g of the compound (7), 0.44 g of 2,3,6, 7,10,11-hexahydroxytriphenylene, and 1.50 g of DMAP dissolved in 60 mL of dichloromethane was stirred at room temperature for 1 hour, then thereto was added, under ice cooling, 2.53 g of DCC dissolved in 20 mL of dichloromethane, followed by stirring under ice cooling for 5 minutes, and stirring overnight at room temperature. The precipitated dicyclohexylurea was filtered off, and the filtrate washed with 3-N hydrochloric acid, a saturated aqueous solution of sodium hydrogen carbonate, and saturated brine, followed by drying over anhydrous sodium sulfate. After evaporating the solvent, the product was purified by silica gel column chromatography and was recrystallized from hexane/ethanol to yield 2.02 g (0.98 mmol) of white solid 2,3,6,7,10, 11-hexakis(4-heptyloxy-2,3,5,6-tetrafluorobenzoyloxy) triphenylene (C).

Phase transition temperature (° C.): Cry 142 Col$_h$ 307 Iso

1H-NMR(CDCl$_3$: δ ppm)8.01(S,6H), 4.34(t, 12H), 1.85 (m, 12H), 1.51(m, 12H), 1.44-1.36(m, 36H), 0.94(t, 18H).

EXAMPLE 4

Synthesis of 2,3,6,7,10,11-hexakis(4-octyloxy-2,3,5, 6-tetrafluorobenzoyloxy)triphenylene (D)

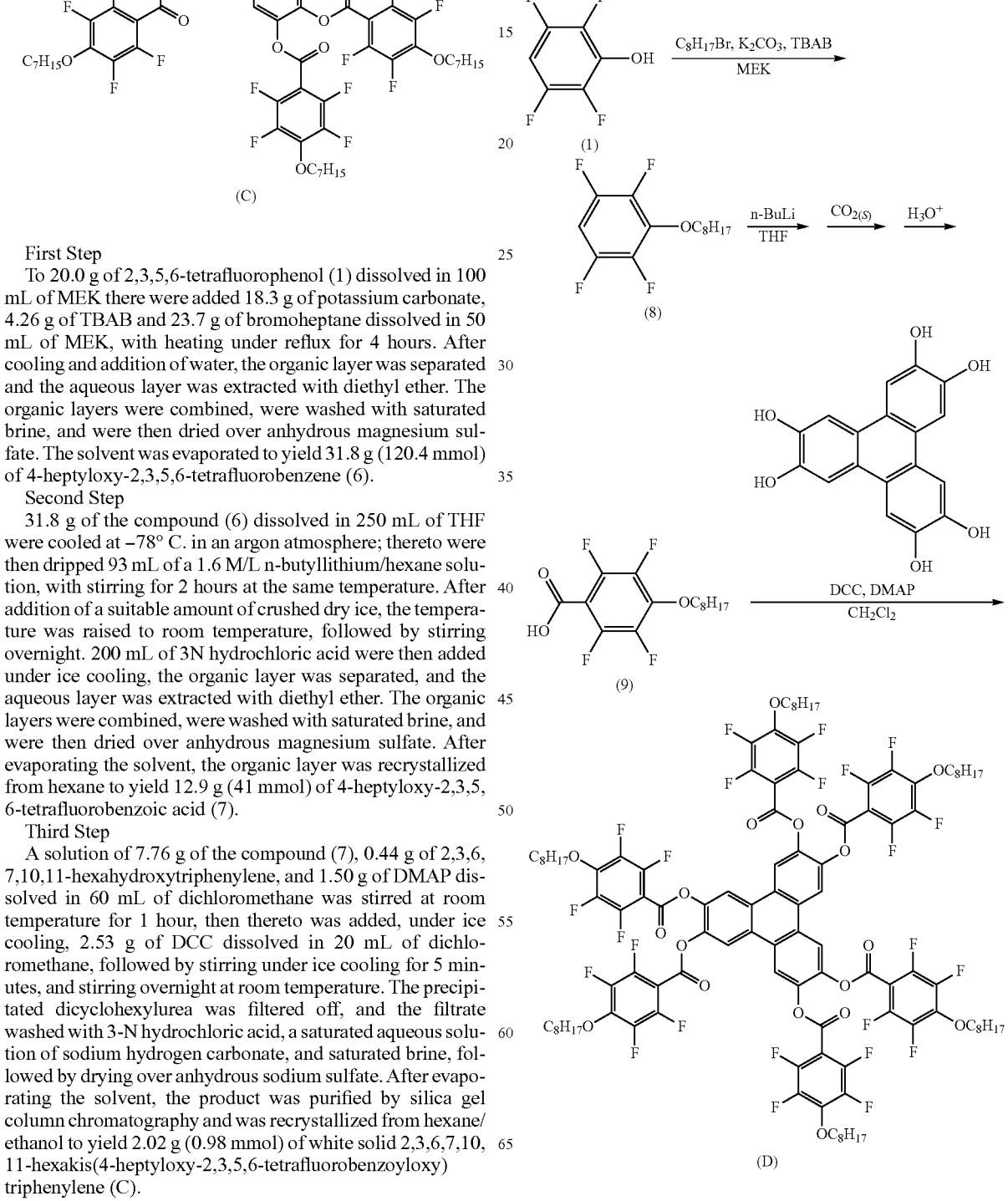

(D)

First Step

To 20.0 g of 2,3,5,6-tetrafluorophenol (1) dissolved in 100 mL of MEK there were added 18.3 g of potassium carbonate, 4.26 g of TBAB and 25.6 g of bromooctane dissolved in 50 mL of MEK, with heating under reflux for 4 hours. After cooling and addition of water, the organic layer was separated and the aqueous layer was extracted with diethyl ether. The organic layers were combined, were washed with saturated brine, and were then dried over anhydrous magnesium sulfate. The solvent was evaporated to yield 33.4 g (120 mmol) of 4-octyloxy-2,3,5,6-tetrafluorobenzene (8).

Second Step 33.4 g of the compound (8) dissolved in 250 mL of THF were cooled at −78° C. in an argon atmosphere; thereto were then dripped 90 mL of a 1.6 M/L n-butyllithium/hexane solution, with stirring for 2 hours at the same temperature. After addition of a suitable amount of crushed dry ice, the temperature was raised to room temperature, followed by stirring overnight. 200 mL of 3N hydrochloric acid were then added under ice cooling, the organic layer was separated, and the aqueous layer was extracted with diethyl ether. The organic layers were combined, were washed with saturated brine, and were then dried over anhydrous magnesium sulfate. After evaporating the solvent, the organic layer was recrystallized from hexane to yield 21.4 g (66 mmol) of 4-octyloxy-2,3,5,6-tetrafluorobenzoic acid (9).

Third Step

A solution of 3.94 g of the compound (9), 0.44 g of 2,3,6,7,10,11-hexahydroxytriphenylene, and 1.50 g of DMAP dissolved in 60 mL of dichloromethane was stirred at room temperature for 1 hour, then thereto was added, under ice cooling, 2.53 g of DCC dissolved in 20 mL of dichloromethane, followed by stirring under ice cooling for 5 minutes, and stirring overnight at room temperature. The precipitated dicyclohexylurea was filtered off, and the filtrate washed with 3-N hydrochloric acid, a saturated aqueous solution of sodium hydrogen carbonate, and saturated brine, followed by drying over anhydrous sodium sulfate. After evaporating the solvent, the product was purified by silica gel column chromatography and was recrystallized from hexane/ethanol to yield 1.44 g (0.67 mmol) of white solid 2,3,6,7,10,11-hexakis(4-octyloxy-2,3,5,6-tetrafluorobenzoyl oxy)triphenylene (D).

Phase transition temperature (° C.): Cry 133 Col$_h$ 308 Iso

1H-NMR(CDCl$_3$: δ ppm)8.00(S, 6H), 4.34(t, 12H), 1.85 (m, 12H), 1.53(m, 12H), 1.39-1.35(m, 48H), 0.94(t, 18H).

EXAMPLE 5

Synthesis of 2,3,6,7,10,11-hexakis(4-decyloxy-2,3,5,6-tetrafluorobenzoyloxy)triphenylene (E)

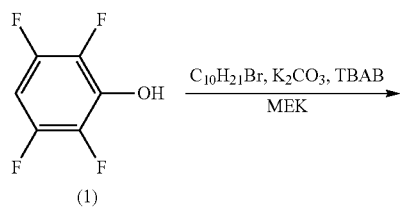

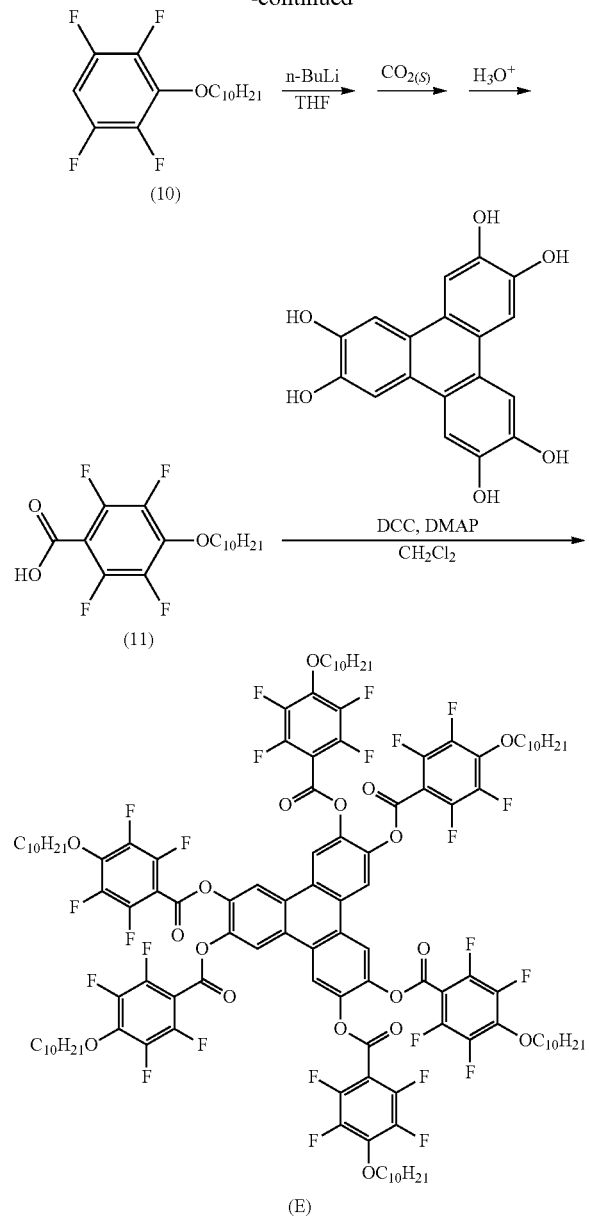

First Step

To 20.0 g of 2,3,5,6-tetrafluorophenol (1) dissolved in 100 mL of MEK there were added 18.3 g of potassium carbonate, 4.26 g of TBAB and 32.0 g of bromodecane dissolved in 50 mL of MEK, with heating under reflux for 4 hours. After cooling and addition of water, the organic layer was separated and the aqueous layer was extracted with diethyl ether. The organic layers were combined, were washed with saturated brine, and were then dried over anhydrous magnesium sulfate. The solvent was evaporated to yield 36.8 g (120 mmol) of 4-decyloxy-2,3,5,6-tetrafluorobenzene (10).

Second Step 36.8 g of the compound (10) dissolved in 250 mL of THF were cooled at −78° C. in an argon atmosphere; thereto were then dripped 100 mL of a 1.6 M/L n-butyllithium/hexane solution, with stirring for 2 hours at the same temperature. After addition of a suitable amount of crushed dry ice, the temperature was raised to room temperature, followed by stirring overnight. 200 mL of 3N hydrochloric acid were then added under ice cooling, the organic layer was separated, and the aqueous layer was extracted with diethyl ether. The organic layers were combined, were washed with saturated brine, and were then dried over anhydrous magnesium sulfate. After evaporating the solvent, the organic layer was recrystallized from hexane to yield 26.5 g (76 mmol) of 4-decyloxy-2,3,5,6-tetrafluorobenzoic acid (11).

Third Step

A solution of 4.29 g of the compound (11), 0.44 g of 2,3,6,7,10,11-hexahydroxytriphenylene, and 1.50 g of DMAP dissolved in 60 mL of dichloromethane was stirred at room temperature for 1 hour, then thereto was added, under ice cooling, 2.53 g of DCC dissolved in 20 mL of dichloromethane, followed by stirring under ice cooling for 5 minutes, and stirring overnight at room temperature. The precipitated dicyclohexylurea was filtered off, and the filtrate washed with 3-N hydrochloric acid, a saturated aqueous solution of sodium hydrogen carbonate, and saturated brine, followed by drying over anhydrous sodium sulfate. After evaporating the solvent, the product was purified by silica gel column chromatography and was recrystallized from hexane/ethanol to yield 1.00 g (0.43 mmol) of white solid 2,3,6,7,10,11-hexakis(4-decyloxy-2,3,5,6-tetrafluorobenzoyl oxy)triphenylene (E).

Phase transition temperature (° C.): Cry 109 Col$_h$ 302 Iso 1H-NMR(CDCl$_3$: δ ppm) 8.07(S,6H), 4.34(t, 12H), 1.84 (m, 12H), 1.51(m, 12H), 1.40-1.31(m, 72H), 0.91(t, 18H).

EXAMPLE 6

Synthesis of 2,3,6,7,10,11-hexakis(4-dodecyloxy-2,3,5,6-tetrafluorobenzoyloxy)triphenylene (F)

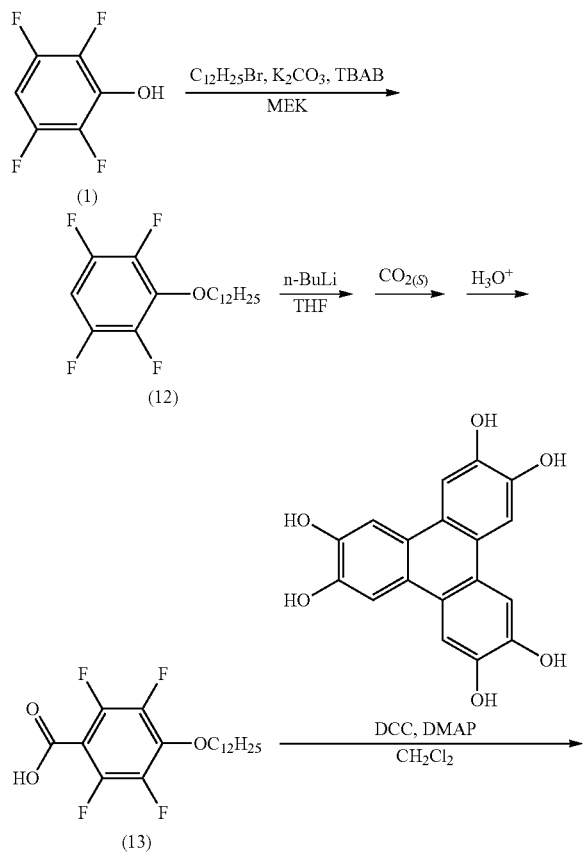

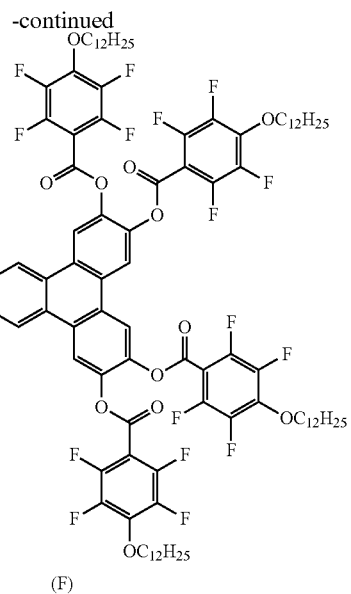

(F)

First Step

To 20.0 g of 2,3,5,6-tetrafluorophenol (1) dissolved in 100 mL of MEK there were added 18.3 g of potassium carbonate, 4.26 g of TBAB and 33.0 g of bromododecane dissolved in 50 mL of MEK, with heating under reflux for 4 hours. After cooling and addition of water, the organic layer was separated and the aqueous layer was extracted with diethyl ether. The organic layers were combined, were washed with saturated brine, and were then dried over anhydrous magnesium sulfate. The solvent was evaporated to yield 40.1 g (120 mmol) of 4-dodecyloxy-2,3,5,6-tetrafluorobenzene (12).

Second Step 40.1 g of the compound (12) dissolved in 250 mL of THF were cooled at −78° C. in an argon atmosphere; thereto were then dripped 95 mL of a 1.6 M/L n-butyllithium/hexane solution, with stirring for 2 hours at the same temperature. After addition of a suitable amount of crushed dry ice, the temperature was raised to room temperature, followed by stirring overnight. 200 mL of 3N hydrochloric acid were then added under ice cooling, the organic layer was separated, and the aqueous layer was extracted with diethyl ether. The organic layers were combined, were washed with saturated brine, and were then dried over anhydrous magnesium sulfate. After evaporating the solvent, the organic layer was recrystallized from hexane to yield 37.5 g (99 mmol) of 4-dodecyloxy-2,3,5,6-tetrafluorobenzoic acid (13).

Third Step

A solution of 4.63 g of the compound (13), 0.44 g of 2,3,6,7,10,11-hexahydroxytriphenylene, and 1.50 g of DMAP dissolved in 60 mL of dichloromethane was stirred at room temperature for 1 hour, then thereto was added, under ice cooling, 2.53 g of DCC dissolved in 20 mL of dichloromethane, followed by stirring under ice cooling for 5 minutes, and stirring overnight at room temperature. The precipitated dicyclohexylurea was filtered off, and the filtrate washed with 3-N hydrochloric acid, a saturated aqueous solution of sodium hydrogen carbonate, and saturated brine, followed by drying over anhydrous sodium sulfate. After evaporating the solvent, the product was purified by silica gel column chromatography and was recrystallized from hexane/ethanol to yield 1.63 g (0.66 mmol) of white solid 2,3,6,7,10,11-hexakis(4-dodecyloxy-2,3,5,6-tetrafluorobenzoyloxy)triphenylene (F).

Phase transition temperature (° C.): Cry 79 Col$_h$ 288 Iso
1H-NMR(CDCl$_3$: δ ppm)8.06(S,6H), 4.34(t, 12H), 1.84 (m, 12H), 1.51(m, 12H), 1.40-1.30(m, 96H), 0.90(t, 18H).

EXAMPLE 7

Synthesis of 2,3,6,7,10,11-hexakis(4-octyloxy-3-fluorobenzoyloxy)triphenylene (G)

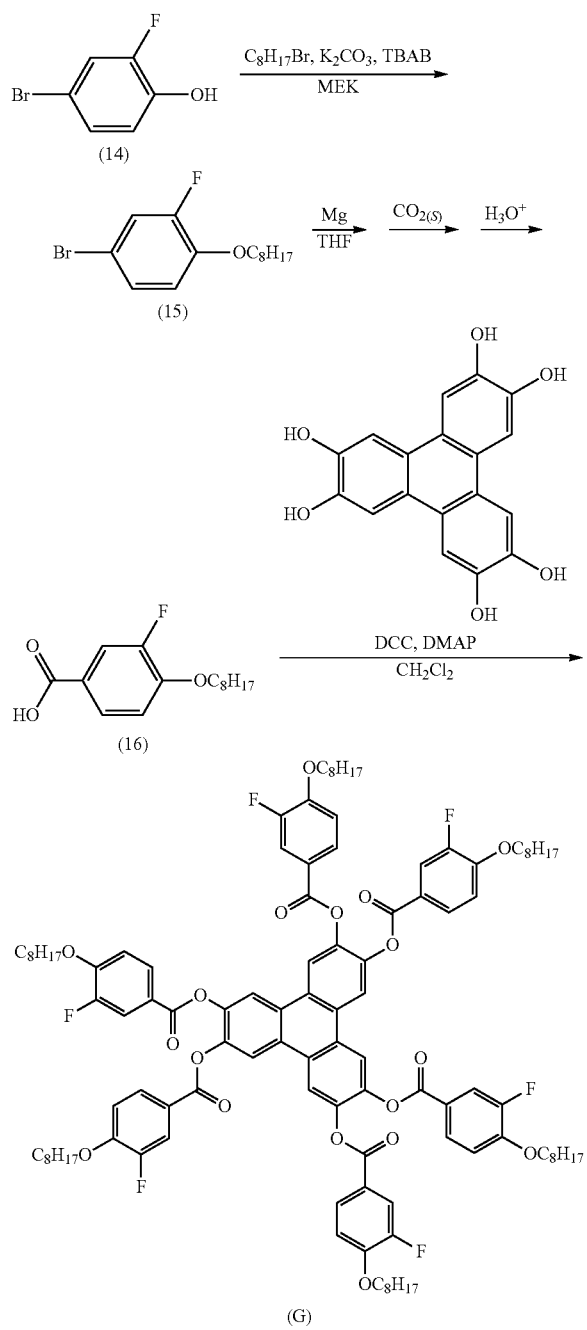

First Step

To 15.0 g of 4-bromo-2-fluorophenol (14) dissolved in 80 mL of MEK there were added 12.0 g of potassium carbonate, 2.79 g of TBAB and 16.7 g of bromooctane dissolved in 40 mL of MEK, with heating under reflux for 4 hours. After cooling and addition of water, the organic layer was separated and the aqueous layer was extracted with diethyl ether. The organic layers were combined, were washed with saturated brine, and were then dried over anhydrous magnesium sulfate. The solvent was evaporated to yield 23.8 g (78.6 mmol) of 4-bromo-2-fluorooctyloxybenzene (15).

Second Step

A small portion of 23.8 g of the compound (15) dissolved in 200 mL of THF was added dropwise initially, in an argon atmosphere, to 2.3 g of dried magnesium; upon checking that reflux had started, dripping of the rest continued slowly. Once dripping was over, heating under reflux continued for 1 hour. Thereafter, the reaction system was cooled to −20° C., under an argon atmosphere, and a suitable amount of crushed dry ice was added thereto, then the temperature was raised to room temperature, followed by stirring overnight. 200 mL of 3N hydrochloric acid were then added under ice cooling, the organic layer was separated, and the aqueous layer was extracted with diethyl ether. The organic layers were combined, were washed with saturated brine, and were then dried over anhydrous magnesium sulfate. After evaporating the solvent, the organic layer was recrystallized from hexane to yield 16.4 g (61.0 mmol) of 4-octyloxy-2-fluorobenzoic acid (16).

Third Step

A solution of 4.38 g of the compound (16), 0.44 g of 2,3,6,7,10,11-hexahydroxytriphenylene, and 1.50 g of DMAP dissolved in 60 mL of dichloromethane was stirred at room temperature for 1 hour, then thereto was added, under ice cooling, 2.53 g of DCC dissolved in 20 mL of dichloromethane, followed by stirring under ice cooling for 5 minutes, and stirring overnight at room temperature. The precipitated dicyclohexylurea was filtered off, and the filtrate washed with 3-N hydrochloric acid, a saturated aqueous solution of sodium hydrogen carbonate, and saturated brine, followed by drying over anhydrous sodium sulfate. After evaporating the solvent, the product was purified by silica gel column chromatography and was recrystallized from hexane/ethanol to yield 1.41 g (0.77 mmol) of white solid 2,3,6,7,10,11-hexakis(4-octyloxy-3-fluorobenzoyloxy)triphenylene (G).

Phase transition temperature (° C.): Cry 56.4 M$_1$ 196.9 M$_2$ 210.2 M$_3$ 235.5 M$_4$ >350 Dec.

1H-NMR(CDCl$_3$: δ ppm)8.01(S,6H), 7.64(d, 6H), 7.48 (dd, 6H), 6.65(t, 6H), 3.96(t, 12H), 1.81(m, 12H), 1.45(m, 12H), 1.34-1.30(m, 48H), 0.89(t, 18H).

EXAMPLE 8

Synthesis of 2,3,6,7,10,11-hexakis(4-octyloxy-2,6-difluorobenzoyloxy)triphenylene (H)

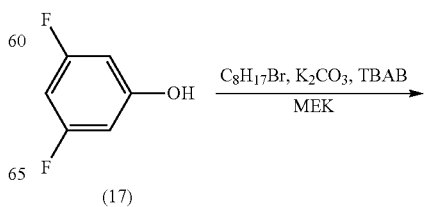

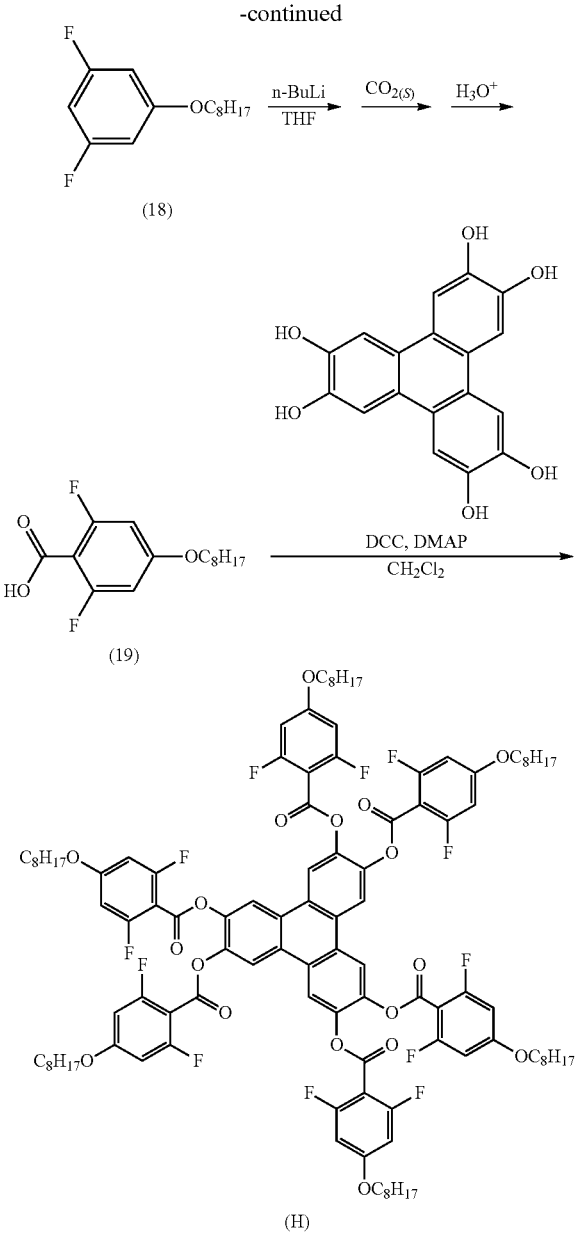

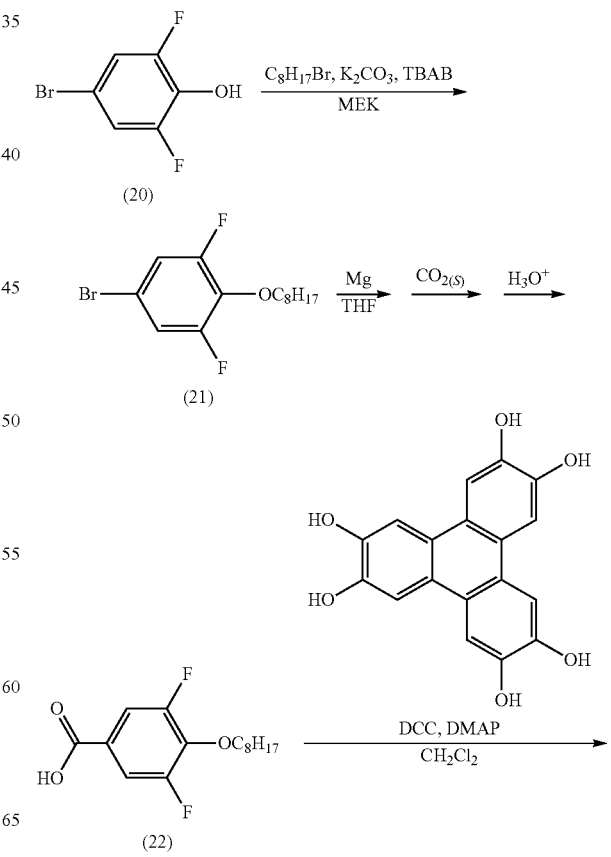

aqueous layer was extracted with diethyl ether. The organic layers were combined, were washed with saturated brine, and were then dried over anhydrous magnesium sulfate. After evaporating the solvent, the organic layer was recrystallized from hexane to yield 17.9 g (62.4 mmol) of 4-octyloxy-2,6-difluorobenzoic acid (19).

Third Step

A solution of 4.67 g of the compound (19), 0.44 g of 2,3,6,7,10,11-hexahydroxytriphenylene, and 1.50 g of DMAP dissolved in 60 mL of dichloromethane was stirred at room temperature for 1 hour, then thereto was added, under ice cooling, 2.53 g of DCC dissolved in 20 mL of dichloromethane, followed by stirring under ice cooling for 5 minutes, and stirring overnight at room temperature. The precipitated dicyclohexylurea was filtered off, and the filtrate washed with 3-N hydrochloric acid, a saturated aqueous solution of sodium hydrogen carbonate, and saturated brine, followed by drying over anhydrous sodium sulfate. After evaporating the solvent, the product was purified by silica gel column chromatography and was recrystallized from hexane/ethanol to yield 1.50 g (0.78 mmol) of white solid 2,3,6,7,10,11-hexakis(4-octyloxy-2,6-difluorobenzoyloxy)tri phenylene (H).

Phase transition temperature (° C.): $Cry_1$ 53.2 $Cry_2$ 115.5 $Col_h$ 176.2 Iso 1H-NMR(CDCl$_3$: δ ppm)8.51(S,6H), 6.49(d,6H), 3.98(t, 12H), 1.80(m, 12H), 1.45(m, 12H), 1.35-1.30(m, 48H), 0.90 (t, 18H).

EXAMPLE 9

Synthesis of 2,3,6,7,10,11-hexakis(4-octyloxy-3,5-difluorobenzoyloxy)triphenylene (I)

First Step

To 15.0 g of 3,5-difluorophenol (17) dissolved in 100 mL of MEK there were added 17.5 g of potassium carbonate, 4.09 g of TBAB and 24.5 g of bromooctane dissolved in 50 mL of MEK, with heating under reflux for 4 hours. After cooling and addition of water, the organic layer was separated and the aqueous layer was extracted with diethyl ether. The organic layers were combined, were washed with saturated brine, and were then dried over anhydrous magnesium sulfate. After evaporating the solvent there were obtained 27.9 g (115 mmol) of 3,5-difluorooctyloxybenzene (18).

Second Step 27.9 g of the compound (18) dissolved in 250 mL of THF were cooled at −78° C. in an argon atmosphere; thereto were then dripped 88 mL of a 1.6 M/L n-butyllithium/hexane solution, with stirring for 2 hours at the same temperature. After addition of a suitable amount of crushed dry ice, the temperature was raised to room temperature, followed by stirring overnight. 200 mL of 3N hydrochloric acid were then added under ice cooling, the organic layer was separated, and the

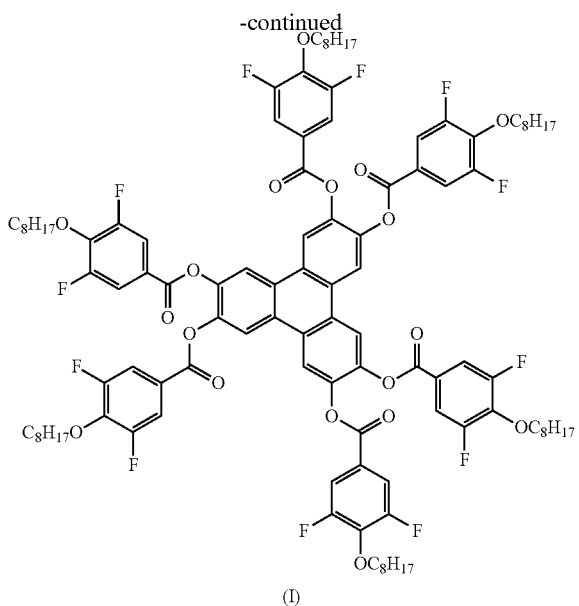

(I)

First Step

To 20.0 g of 4-bromo-2,6-difluorophenol (20) dissolved in 80 mL of MEK there were added 13.2 g of potassium carbonate, 3.09 g of TBAB and 18.5 g of bromooctane dissolved in 40 mL of MEK, with heating under reflux for 4 hours. After cooling and addition of water, the organic layer was separated and the aqueous layer was extracted with diethyl ether. The organic layers were combined, were washed with saturated brine, and were then dried over anhydrous magnesium sulfate. The solvent was evaporated to yield 25.3 g (79.0 mmol) of 4-bromo-2,6-difluorooctyloxybenzene (21).

Second Step

A small portion of 23.8 g of the compound (15) dissolved in 200 mL of THF was added dropwise initially, in an argon atmosphere, to 2.3 g of dried magnesium; upon checking that reflux had started, dripping of the rest continued slowly. Once dripping was over, heating under reflux continued for 1 hour. Thereafter, the reaction system was cooled to −20° C., under an argon atmosphere, and a suitable amount of crushed dry ice was added thereto, then the temperature was raised to room temperature, followed by stirring overnight. 200 mL of 3N hydrochloric acid were then added under ice cooling, the organic layer was separated, and the aqueous layer was extracted with diethyl ether. The organic layers were combined, were washed with saturated brine, and were then dried over anhydrous magnesium sulfate. After evaporating the solvent, the organic layer was recrystallized from hexane to yield 8.98 g (31.4 mmol) of 4-octyloxy-3,5-difluorobenzoic acid (22).

Third Step

A solution of 4.67 g of the compound (22), 0.44 g of 2,3,6,7,10,11-hexahydroxytriphenylene, and 1.50 g of DMAP dissolved in 60 mL of dichloromethane was stirred at room temperature for 1 hour, then thereto was added, under ice cooling, 2.53 g of DCC dissolved in 20 mL of dichloromethane, followed by stirring under ice cooling for 5 minutes, and stirring overnight at room temperature. The precipitated dicyclohexylurea was filtered off, and the filtrate washed with 3-N hydrochloric acid, a saturated aqueous solution of sodium hydrogen carbonate, and saturated brine, followed by drying over anhydrous sodium sulfate. After evaporating the solvent, the product was purified by silica gel column chromatography and was recrystallized from hexane/ethanol to yield 1.75 g (0.91 mmol) of white solid 2,3,6,7,10,11-hexakis(4-octyloxy-2,5-difluorobenzoyloxy)tri phenylene (I).

Phase transition temperature (° C.): $Cry_1$ 14.8 $Cry_2$ 139.8 $Col_h$>350 Dec.

1H-NMR(CDCl$_3$: δ ppm)8.06(S,6H), 7.38(d,6H), 4.19(t, 12H), 1.76(m, 12H), 1.45(m, 12H), 1.34-1.30(m, 48H), 0.90 (t, 18H).

EXAMPLE 10

The compounds below were prepared on the basis of the methods from Examples 1 to 9 and synthesis methods described in the literature.

TABLE 1

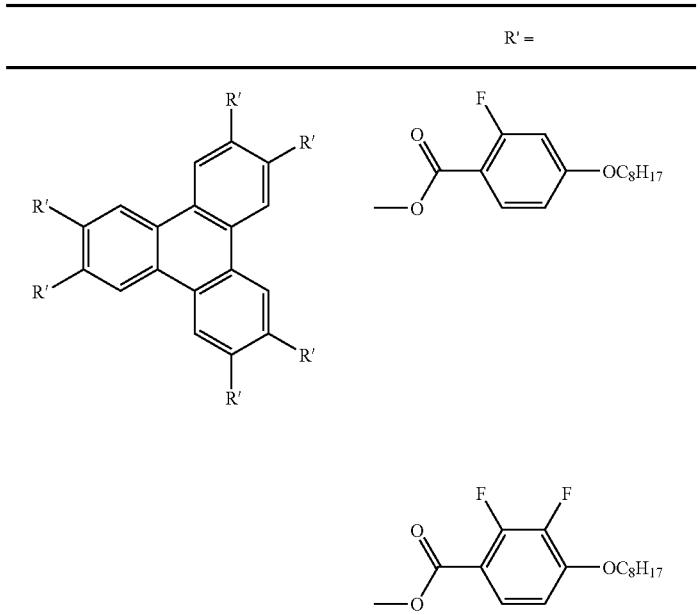

TABLE 1-continued
| R' = |
|---|
| 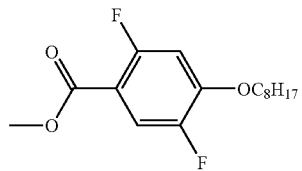 |
| 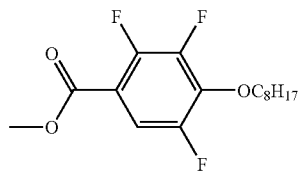 |
| 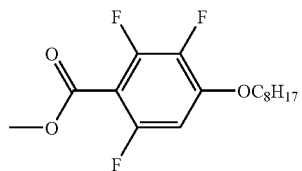 |
| 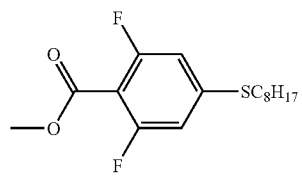 |
| 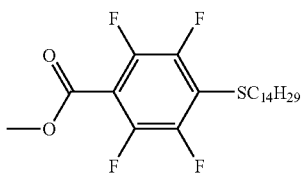 |
| 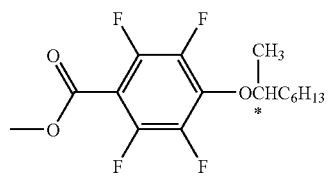 |
| 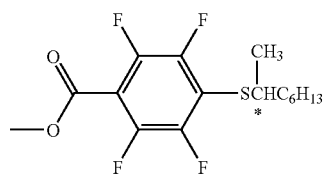 |
| 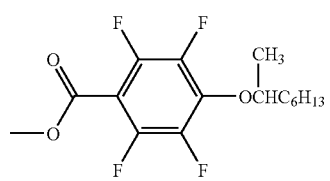 |

TABLE 1-continued
| R' = |
|---|
| 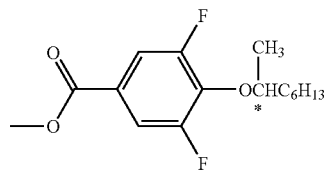 |
| 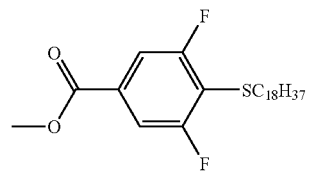 |
| 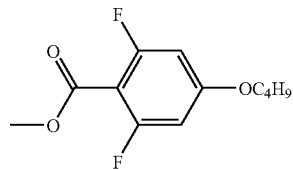 |
| 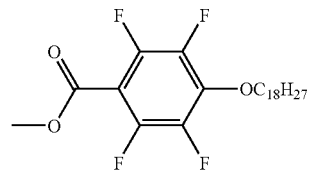 |
| 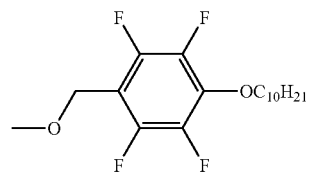 |
| 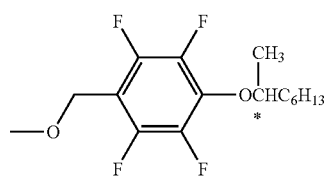 |
| 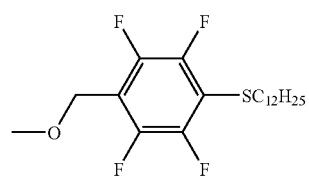 |
| 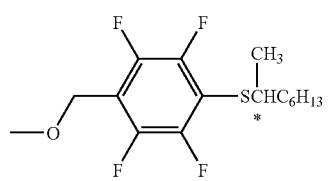 |

TABLE 1-continued
| R' = |
|---|
| 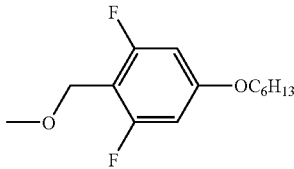 |
| 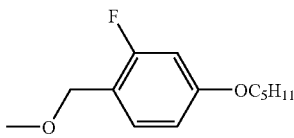 |
| 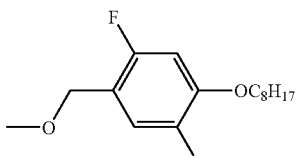 |
| 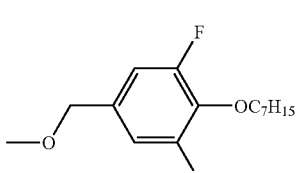 |
| 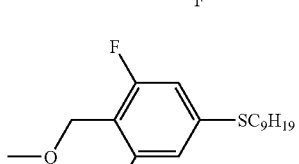 |
| 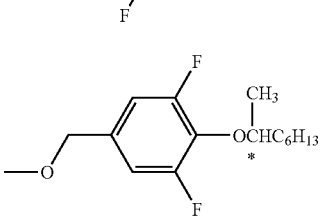 |
| 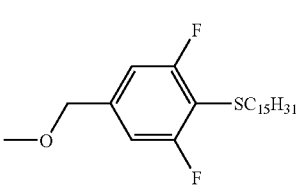 |
| 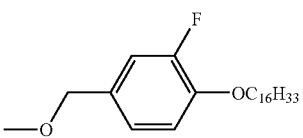 |
| 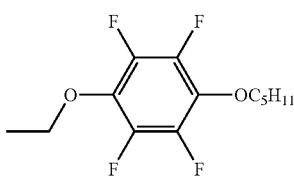 |

TABLE 1-continued
R' =
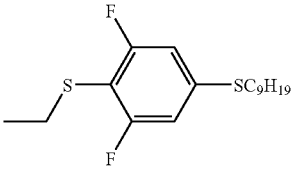
TABLE 2
R' =
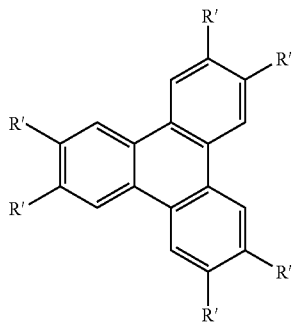

TABLE 2-continued

| R' = |
|---|

TABLE 2-continued
| R' = |
|---|
| 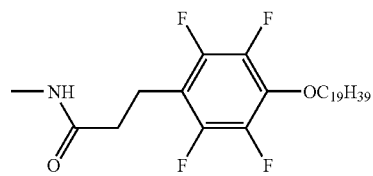 |
| 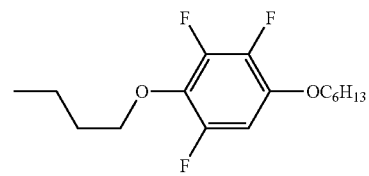 |
| 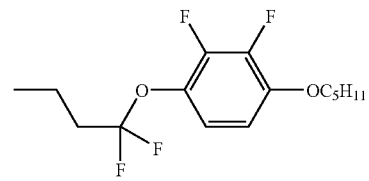 |
| 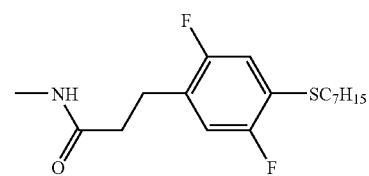 |
| 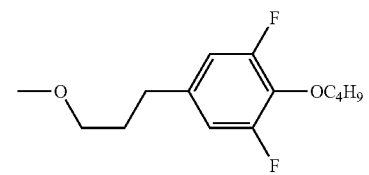 |
| 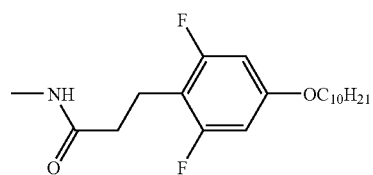 |
| 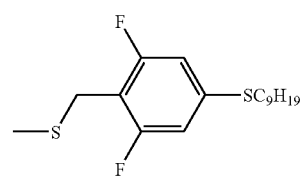 |
| 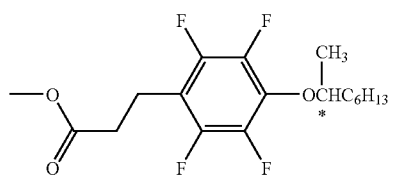 |

TABLE 2-continued

R' =

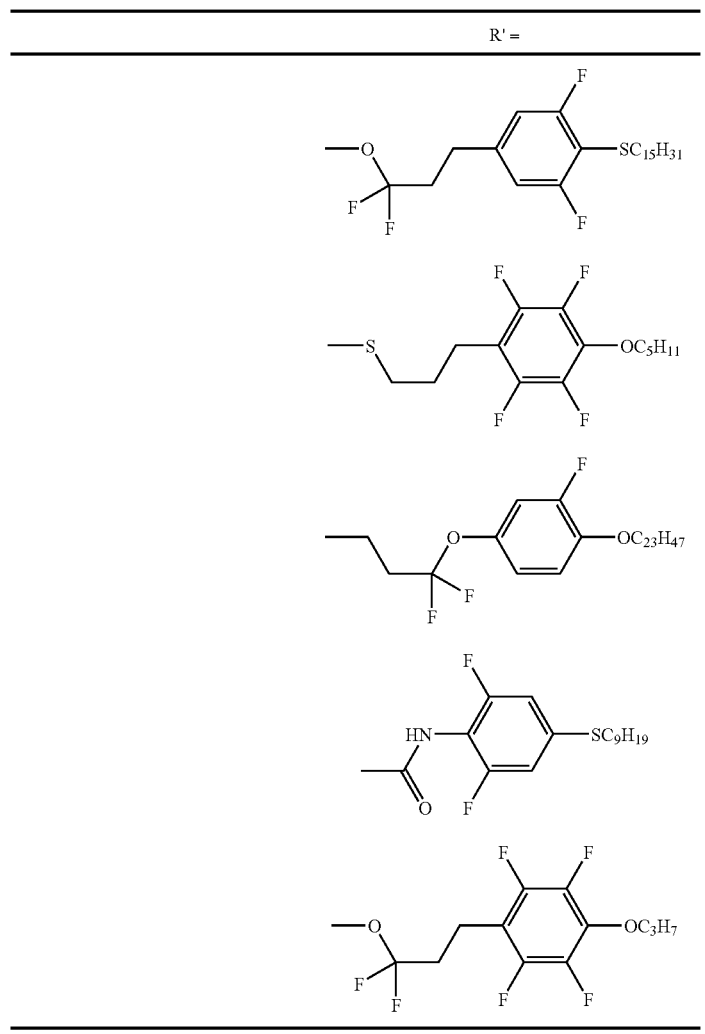

EXAMPLE 11

Measurement of the carrier mobility of the compound (F)

A TOF measurement cell was manufactured that comprised a thin film layer of the compound (F) that can be prepared as in Example 6. Firstly, a spacer was spread on a glass substrate having an ITO electrode. Thereon was bonded a further glass substrate having an ITO electrode, to manufacture a TOF measurement cell. The cell was heated up to 288° C., and then a crystal of the compound (F) was melted by being brought into contact with the gap between the two substrates, diffusing rapidly within the cell on account of capillarity. The compound (F) solidified then upon bringing the cell back to room temperature. The cell is illustrated schematically in FIG. 1.

Conducting wires were attached to the cell, which was then set in a temperature-variable hot stage. Voltage was applied to the measurement cell, then nanosecond pulses of nitride laser (wavelength: 337 nm) were irradiated onto the sample, and the changes over time in the generated current were measured with an oscilloscope.

The time-varying waveform of electric current was measured employing the method by Harvey Scher and Elliott W. Montroll, Phys. Rev. B, 12, 2455 (1975). The time (t) taken by a carrier to reach the counterelectrode from the electrode irradiated by the laser pulse light was determined based on that waveform. Carrier mobility was then calculated based on the time (t) taken by a carrier to reach the counterelectrode, the applied voltage and the electrode spacing.

The positive hole mobility at 180° C., where the compound (F) exhibits a $Col_h$ phase, was of $1.4 \times 10^{-3}$ cm$^2$/V·S, for an electrode spacing of 7.98 μm and an applied voltage of 40V.

COMPARATIVE EXAMPLE 1

The characteristic values of the materials (B) to (E) of the present invention prepared in Examples 2 to 5 were compared against those of compounds having a similar structure but lacking fluorinated benzene rings, described by N. H. Tinh et al, Molecular Crystal Liquid Crystal, 1981, 68, 101.

The conventional compounds no fluorinated benzene rings, described in the literature, did not exhibit a $Col_h$ phase, and the temperature range at which they manifested a liquid crystal phase was not more than 100° C. By contrast, the material of the present invention manifested a $Col_h$ phase that had a wide temperature range ($C_6H_{13}O$: 144° C., $C_7H_{15}O$: 165° C., $C_8H_{17}O$: 175° C., $C_{10}H_{21}O$: 193° C.). This evidenced, based on comparison that introducing a fluorinated phenylene ring resulted in a wider temperature range of the $Col_h$ phase.

The clearing point in compounds no fluorinated benzene rings decreases as the terminal chains become longer ($C_6H_{13}O$: 274° C., $C_7H_{15}O$: 253° C., $C_8H_{17}O$: 244° C., $C_{10}H_{21}O$: 212° C.); in the material of the present invention, however, the clearing point remains high ($C_6H_{13}O$: 301° C., $C_7H_{15}O$: 307° C., $C_8H_{17}O$: 308° C., $C_{10}H_{21}O$: 302° C.) irrespective of the chain length of the terminal chains. This showed, based on comparison that introducing a fluorinated phenylene ring resulted in substantial enhancement of the thermal stability of the $Col_h$ phase.

Based on comparison, thus, the above results indicate that introducing a fluorinated phenylene ring resulted in a largely wider temperature range and largely enhanced thermal stability of the $Col_h$ phase.

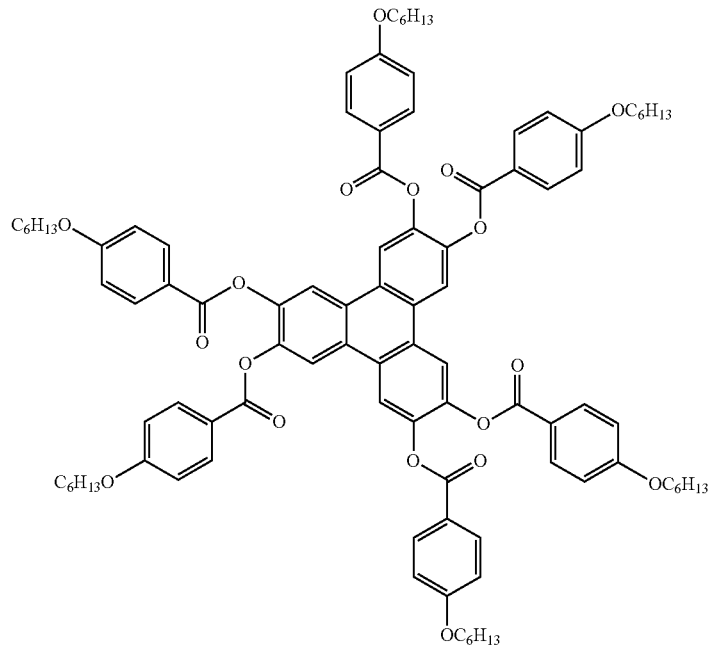

Cry 186 $D_t$ 193 $N_D$ 274 Iso (° C.)

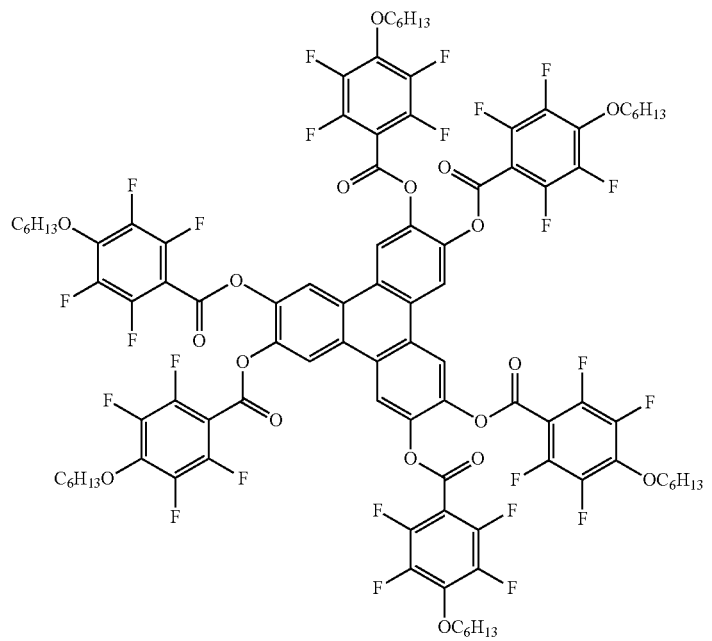

$Cry_1$ 130 $Cry_2$ 157 $Col_h$ 301 Iso (° C.)

-continued
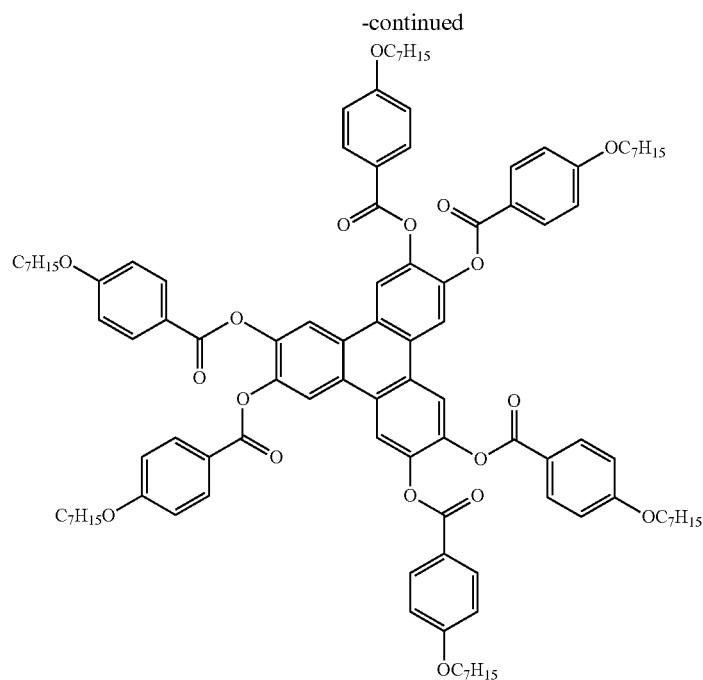
Cry 168 N_D 253 Iso (° C.)
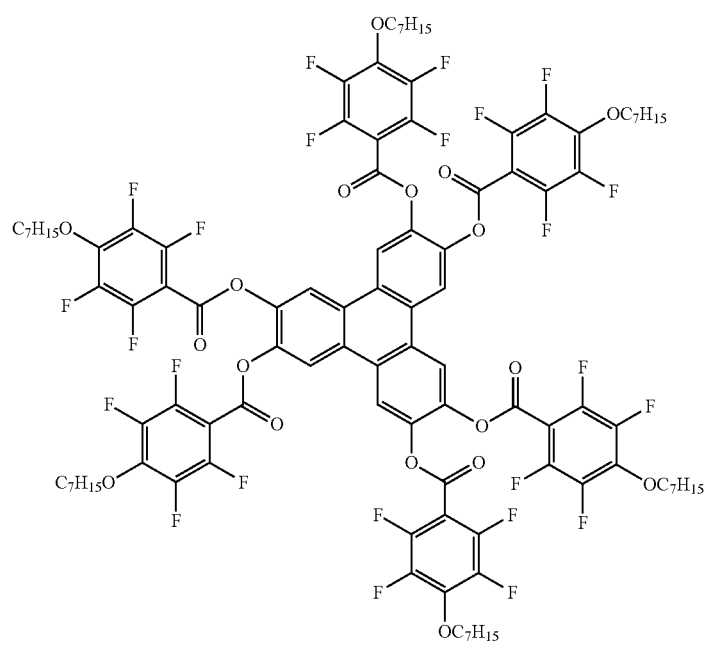
(C)
Cry 142 Col_h 307 Iso (° C.)

-continued
(D)
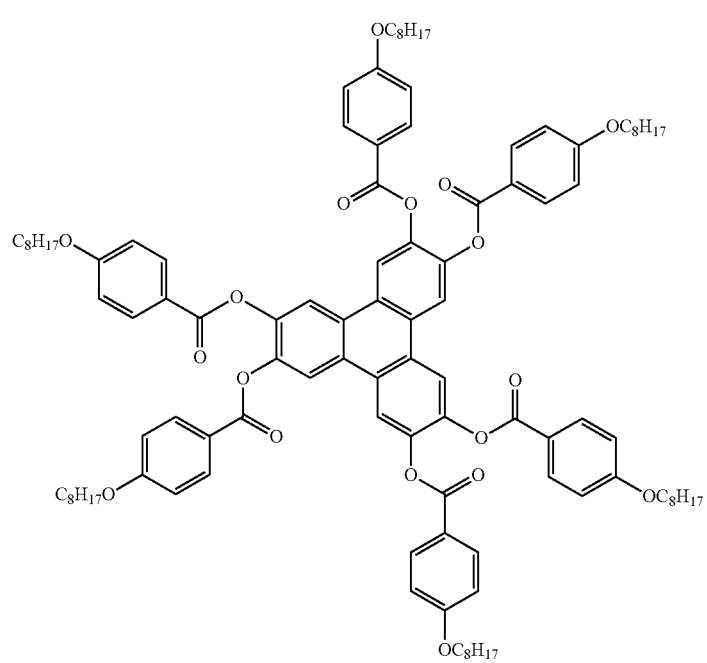
Cry 152 D$_r$ 168 N$_D$ 244 Iso (° C.)
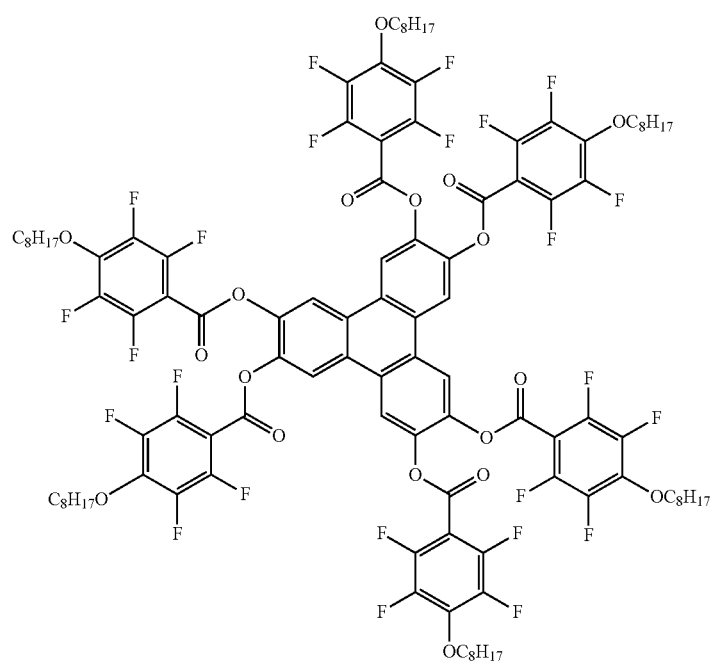
Cry 133 Col$_h$ 308 Iso (° C.)

-continued
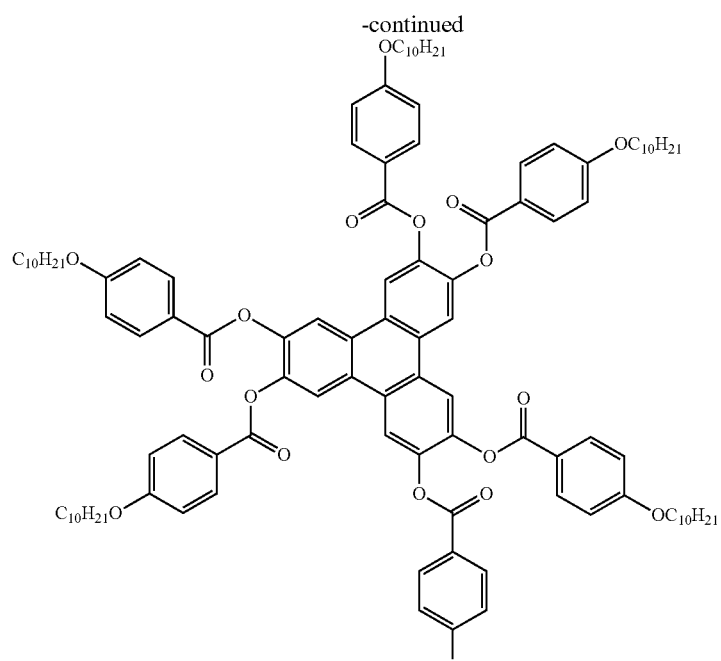
Cry 142 D$_r$ 191 N$_D$ 212 Iso (° C.)
(E)
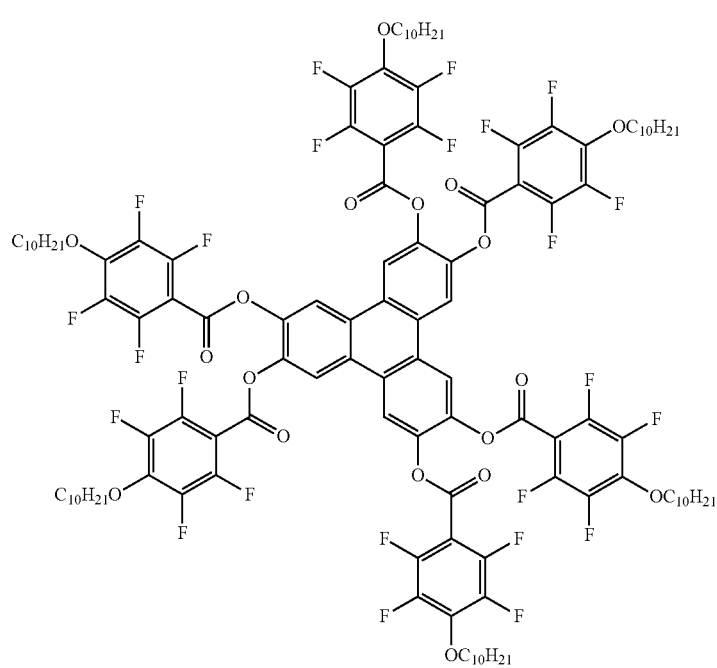
Cry 109 Col$_h$ 302 Iso (° C.)

What is claimed is:

1. A liquid crystalline organic semiconductor material having substituents on the periphery of a rigid plate-like central structure, wherein the substituents have a fluorinated phenylene group and columns in which a liquid crystalline compound is accumulated in a stack and are aligned in the shape of a hexagonal crystal, comprising at least one compound selected from the group of compounds represented by formula (1):

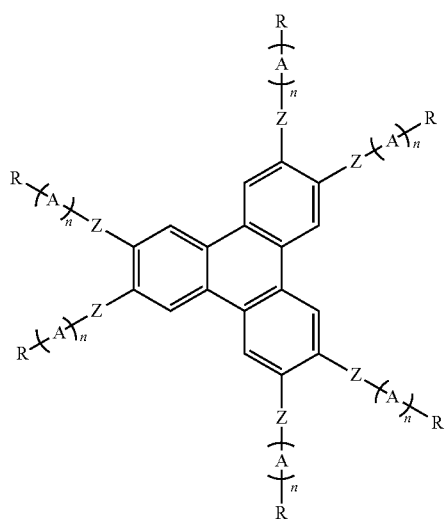

(1)

in formula (1), R is independently hydrogen, a C12 to C24 linear or branched alkyl; in the alkyl, any —CH$_2$— may be replaced by —O—, and —CO—, any —(CH$_2$)$_2$— may be replaced by —CH=CH— or —C≡C—, and any hydrogen may be replaced by a halogen;

A is independently 1,4-phenylene in which any hydrogen is replaced by fluorine;

Z is independently a single bond, —(CH$_2$)$_2$—, —COO—, —OCO—, —CONH—, —NHCO—, —CH$_2$O—, —OCH$_2$—, —CF$_2$O—, —OCF$_2$—, —CH=CH—, —C≡C—, —CF=CF—, —CH$_2$CO—, or —COCH$_2$; and n is 1.

2. The liquid crystalline organic semiconductor material according to claim 1, wherein in formula (1), R is hydrogen, a C12 to C20 linear or branched alkyl, C12 to C20 linear or branched alkoxy, C12 to C20 linear or branched alkenyl, C12 to C20 linear or branched alkynyl, C12 to C20 linear or branched alkoxyalkyl, or C12 to C20 linear or branched alkenyloxy, and any hydrogen in these groups may be replaced by fluorine;

A is independently 2-fluoro-1,4-phenylene, 2,3-difluoro-1,4-phenylene, 2,6-difluoro-1,4-phenylene, 2,3,5-trifluoro-1,4-phenylene, or 2,3,5,6-tetrafluoro-1,4-phenylene;

and Z is independently a single bond, —(CH$_2$)$_2$—, —COO—, —OCO—, —CONH—, —NHCO—, —CH$_2$O—, —OCH$_2$—, —CH=CH—, —C≡C—, or —CF=CF—.

3. The liquid crystalline organic semiconductor material according to claim 1, comprising at least one compound selected from the group of compounds represented by formula (2):

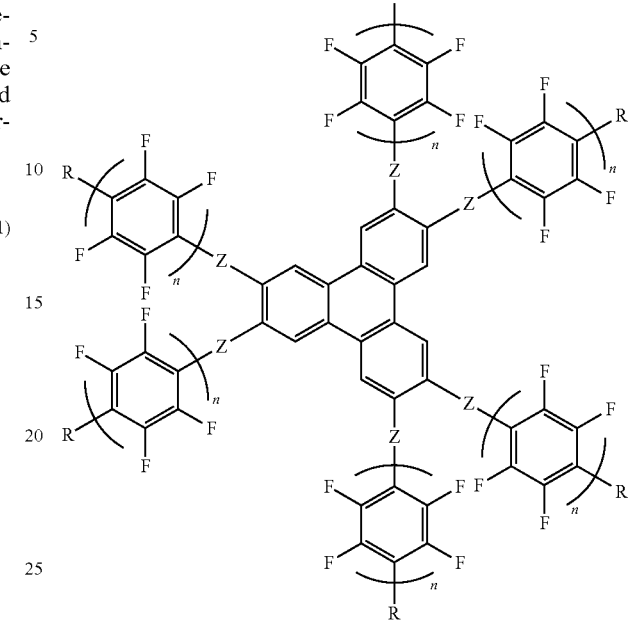

(2)

in formula (2), R is a C12 to C24 linear or branched alkyl, C12 to C23 linear or branched alkoxy, C12 to C24 linear or branched alkenyl, C12 to C24 linear or branched alkynyl, C12 to C23 linear or branched alkoxyalkyl, or C12 to C23 linear or branched alkenyloxy, and any hydrogen in these groups may be replaced by fluorine;

Z is independently a single bond, —(CH$_2$)$_2$—, —COO—, —OCO—, —CONH—, —NHCO—, —CH$_2$O—, —OCH$_2$—, —CH=CH—, —C≡C—, or —CF=CF—;

and n is 1.

4. The liquid crystalline organic semiconductor material according to claim 1, comprising at least one compound selected from the group of compounds represented by formula (3):

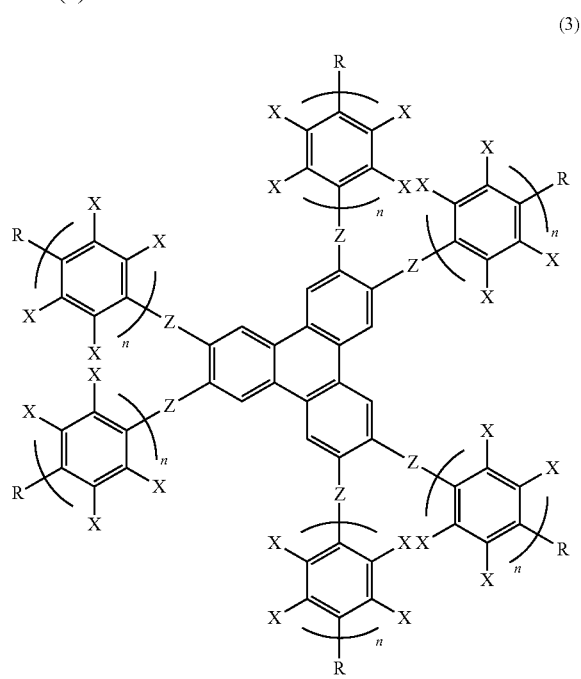

(3)

in formula (3), R is a C12 to C24 linear or branched alkyl, C12 to C23 linear or branched alkoxy, C12 to C24 linear or branched alkenyl, C12 to C24 linear or branched alkynyl, C12 to C23 linear or branched alkoxyalkyl, or C12 to C23 linear or branched alkenyloxy, and any hydrogen in these groups may be replaced by fluorine;

Z is independently a single bond, —(CH$_2$)$_2$—, —COO—, —OCO—, —CONH—, —NHCO—, —CH$_2$O—, —OCH$_2$—, —CH=CH—, —C≡C—, or —CF=CF—;

X is independently hydrogen or fluorine but not all X are hydrogen or fluorine;

and n is 1.

5. At least one compound selected from the group of compounds represented by formula (4):

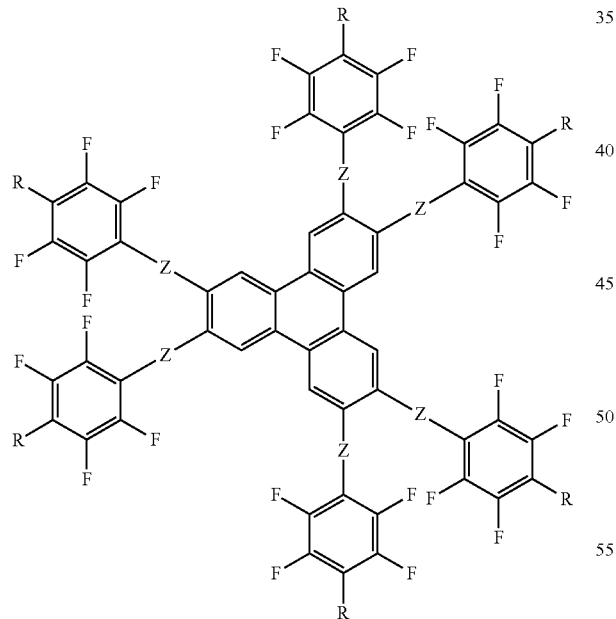

(4)

in formula (4), R is independently a C12 to C20 linear or branched alkyl, C12 to C20 linear or branched alkoxy, C12 to C20 linear or branched alkenyl, C12 to C20 linear or branched alkynyl, C12 to C20 linear or branched alkoxyalkyl, or C12 to C20 linear or branched alkenyloxy;

and Z is independently a single bond, —(CH$_2$)$_2$—, —CONH—, —NHCO—, —CH$_2$O—, —OCH$_2$—, —CH=CH—, —C≡C—, or —CF=CF.

6. At least one compound selected from the group of compounds represented by formula (5):

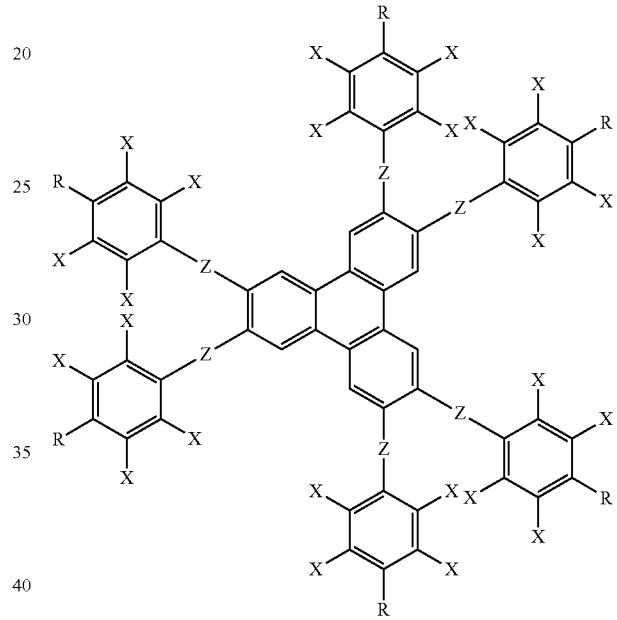

(5)

in formula (5), R is independently a C12 to C20 linear or branched alkyl, C12 to C20 linear or branched alkoxy, C12 to C20 linear or branched alkenyl, C12 to C20 linear or branched alkynyl, C12 to C20 linear or branched alkoxyalkyl, or C12 to C20 linear or branched alkenyloxy;

and Z is independently a single bond, —(CH$_2$)$_2$—, —CONH—, —NHCO—, —CH$_2$O—, —OCH$_2$—, —CH=CH—, —C≡—, or —CF=CF.

and X is independently hydrogen or fluorine but not all X are hydrogen or fluorine.

7. At least one compound selected from the group of compounds represented by formula (6):

(6)

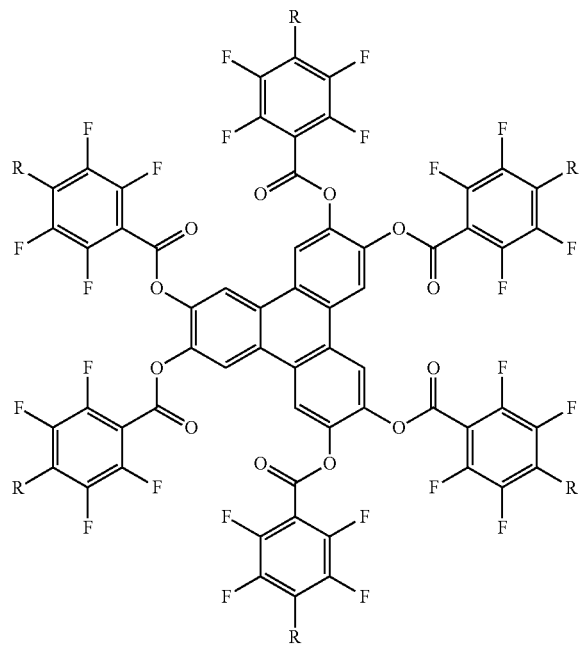

in formula (6), R is a C12 to C24 linear or branched alkyl, C12 to C23 linear alkoxy, C12 to C23 branched alkoxy, or C12 to C24 linear or branched alkenyl.

8. At least one compound selected from the group of compounds represented by formula (7):

(7)

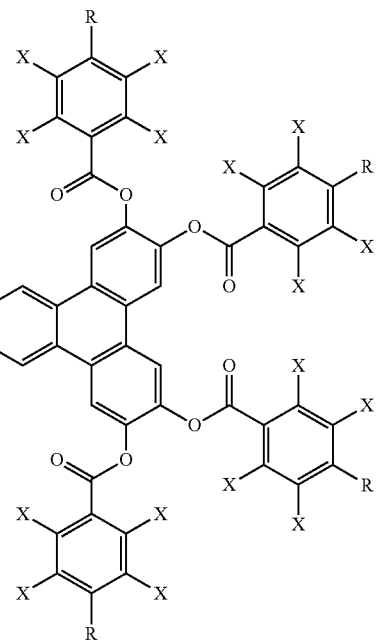

in formula (7), R is a C12 to C24 linear or branched alkyl, C1 to C9 linear alkoxy, C12 to C23 linear alkoxy, C12 to C23 branched alkoxy, or C12 to C24 linear or branched alkenyl;

and X is independently hydrogen or fluorine but not all X are hydrogen or fluorine.

9. A composition containing the liquid crystalline organic semiconductor material according to claim 1 and a substrate.

10. A composition containing the compound according to claim 5.

11. A resin composition comprising the liquid crystalline organic semiconductor material according to claim 1 and a synthetic organic polymer.

\* \* \* \* \*